United States Patent
Clark et al.

(10) Patent No.: US 7,311,011 B2
(45) Date of Patent: Dec. 25, 2007

(54) APPARATUSES FOR INTERACTION WITH A SUBTERRANEAN FORMATION, AND METHODS OF USE THEREOF

(75) Inventors: Don T. Clark, Idaho Falls, ID (US); Richard L. Jones, Idaho Falls, ID (US); Terry D. Turner, Idaho Falls, ID (US); Joel M. Hubbell, Idaho Falls, ID (US); James B. Sisson, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 24 days.

(21) Appl. No.: 10/995,799

(22) Filed: Nov. 22, 2004

(65) Prior Publication Data

US 2005/0120813 A1 Jun. 9, 2005

Related U.S. Application Data

(60) Continuation-in-part of application No. 10/973,710, filed on Oct. 25, 2004, now Pat. No. 6,938,503, and a continuation-in-part of application No. 10/910,860, filed on Aug. 3, 2004, now abandoned, which is a continuation-in-part of application No. 10/873,975, filed on Jun. 22, 2004, now Pat. No. 6,976,386, which is a continuation-in-part of application No. 10/376,153, filed on Feb. 28, 2003, now Pat. No. 6,920,780, which is a continuation-in-part of application No. 10/285,835, filed on Nov. 1, 2002, now Pat. No. 6,820,701, which is a division of application No. 10/285,798, filed on Oct. 31, 2002, now Pat. No. 6,826,972, which is a division of application No. 10/285,786, filed on Oct. 31, 2002, now abandoned, which is a division of application No. 10/286,709, filed on Oct. 31, 2002, now Pat. No. 6,772,621.

(51) Int. Cl.
*G01N 1/10* (2006.01)

(52) U.S. Cl. .................................. 73/864.74
(58) Field of Classification Search ............ 73/864.74, 73/866.5; 403/348
See application file for complete search history.

(56) References Cited

U.S. PATENT DOCUMENTS 2,150,221 A 3/1939 Hinderliter (Continued)

FOREIGN PATENT DOCUMENTS

| GB | 2137760 A | 10/1984 |
| GB | 2249182 A | 4/1992 |
| JP | 63030743 A | 2/1988 |
| WO | WO 9804915 A1 | 2/1998 |

OTHER PUBLICATIONS

U.S. Appl. No. 10/873,975, filed Jun. 22, 2004, entitled "Tensiometer Methods.".

(Continued)

*Primary Examiner*—Hezron Williams
*Assistant Examiner*—John Fitzgerald
(74) *Attorney, Agent, or Firm*—Trask Britt

(57) ABSTRACT

An access casing assembly structured for placement at least partially within a subterranean formation by forcing the access casing assembly thereinto, comprising a plurality of casing sections operably coupled to form a central elongated cavity for providing access to the subterranean region is disclosed. Further, a tip portion of the access casing assembly may include a porous filter through which liquid or gas may communicate with the central elongated cavity. Also, a receiving member or at least one engagement hub may form a portion of the central elongated cavity and may include an engagement feature configured for selectively and lockingly engaging a locking structure of a device to be positioned within the access casing assembly. Methods of use are disclosed. A tensiometer is disclosed including a chamber structured for allowing at least partially filling with a fluid subsequent to contact therewith.

50 Claims, 19 Drawing Sheets

U.S. PATENT DOCUMENTS

| | | | |
|---|---|---|---|
| 2,617,166 A * | 11/1952 | Kaufmann | 24/590.1 |
| 3,043,133 A | 7/1962 | Richards | |
| 3,049,914 A | 8/1962 | Richards | |
| 3,103,117 A | 9/1963 | Richards | |
| 3,367,620 A * | 2/1968 | Holt | 249/213 |
| 3,659,882 A | 5/1972 | Souresny | |
| 3,815,380 A * | 6/1974 | Esmay | 464/173 |
| 3,871,211 A | 3/1975 | Tal | |
| 3,898,872 A | 8/1975 | Skaling | |
| 3,910,300 A | 10/1975 | Tal | |
| 3,939,699 A | 2/1976 | McCormick | |
| 3,961,753 A | 6/1976 | Sears | |
| 3,992,095 A | 11/1976 | Jacoby et al. | |
| 4,068,525 A | 1/1978 | Skaling | |
| 4,137,931 A | 2/1979 | Hasenbeck | |
| 4,295,801 A | 10/1981 | Bennett | |
| 4,332,160 A | 6/1982 | Baragar et al. | |
| 4,410,204 A | 10/1983 | Reimert | |
| 4,655,076 A | 4/1987 | Weihe et al. | |
| 4,669,554 A | 6/1987 | Cordry | |
| 4,679,422 A | 7/1987 | Rubin et al. | |
| 4,759,227 A | 7/1988 | Timmons | |
| 4,768,258 A * | 9/1988 | Langenstein | 16/429 |
| 4,768,588 A * | 9/1988 | Kupsa | 166/55 |
| 4,804,050 A * | 2/1989 | Kerfoot | 175/20 |
| 4,807,707 A * | 2/1989 | Handley et al. | 175/20 |
| 4,845,978 A | 7/1989 | Whitford | |
| 4,922,945 A | 5/1990 | Browne | |
| 4,923,333 A | 5/1990 | Timmons | |
| 4,986,690 A * | 1/1991 | Cooksey | 403/319 |
| 5,000,051 A | 3/1991 | Bredemeier | |
| 5,015,162 A * | 5/1991 | Heppner | 418/48 |
| 5,035,149 A | 7/1991 | Wierenga | |
| 5,046,568 A | 9/1991 | Cordry | |
| 5,123,492 A | 6/1992 | Lizanec et al. | |
| 5,128,882 A | 7/1992 | Cooper et al. | |
| 5,149,149 A * | 9/1992 | Wu | 285/402 |
| 5,156,179 A | 10/1992 | Peterson et al. | |
| 5,168,765 A | 12/1992 | Broussard | |
| 5,179,347 A | 1/1993 | Hawkins | |
| 5,272,910 A | 12/1993 | Everett et al. | |
| 5,327,981 A * | 7/1994 | Morgan | 175/21 |
| 5,335,731 A | 8/1994 | Ringgenberg et al. | |
| 5,337,838 A | 8/1994 | Sorensen | |
| 5,358,057 A * | 10/1994 | Peters et al. | 175/20 |
| 5,402,165 A | 3/1995 | Linville et al. | |
| 5,435,176 A | 7/1995 | Manchak | |
| 5,439,800 A | 8/1995 | Thompson | |
| 5,465,628 A | 11/1995 | Timmons | |
| 5,481,927 A | 1/1996 | Hubbell et al. | |
| 5,487,431 A | 1/1996 | Webb | |
| 5,503,031 A | 4/1996 | Scott et al. | |
| 5,520,248 A | 5/1996 | Sisson et al. | |
| 5,553,492 A | 9/1996 | Barrett et al. | |
| 5,567,889 A | 10/1996 | Sullivan et al. | |
| 5,587,538 A * | 12/1996 | Bratton | 73/863.33 |
| 5,589,825 A | 12/1996 | Pomerleau | |
| 5,635,653 A | 6/1997 | Wittig et al. | |
| 5,644,947 A | 7/1997 | Hubbell et al. | |
| 5,677,499 A | 10/1997 | Sullivan et al. | |
| 5,739,536 A | 4/1998 | Bucholtz et al. | |
| 5,758,538 A | 6/1998 | Hubbell et al. | |
| 5,785,357 A | 7/1998 | Foster et al. | |
| 5,803,186 A | 9/1998 | Berger et al. | |
| 5,804,743 A | 9/1998 | Vroblesky et al. | |
| 5,864,069 A | 1/1999 | Sullivan et al. | |
| 5,878,646 A | 3/1999 | Schewe | |
| 5,889,217 A | 3/1999 | Rossabi et al. | |
| 5,902,939 A | 5/1999 | Ballard et al. | |
| 5,915,476 A | 6/1999 | Hubbell et al. | |
| 5,921,328 A | 7/1999 | Babineau et al. | |
| 5,941,121 A | 8/1999 | Faybishenko | |
| 5,969,242 A | 10/1999 | Hubbell et al. | |
| 6,115,061 A | 9/2000 | Lieberman et al. | |
| 6,151,810 A * | 11/2000 | Mukai | 37/350 |
| 6,208,940 B1 | 3/2001 | Kram et al. | |
| 6,230,820 B1 * | 5/2001 | Cordry | 175/20 |
| 6,236,941 B1 | 5/2001 | Kram et al. | |
| 6,263,726 B1 | 7/2001 | Hubbell et al. | |
| 6,289,725 B1 | 9/2001 | Hubbell et al. | |
| 6,308,563 B1 | 10/2001 | Hubbell et al. | |
| 6,318,190 B1 | 11/2001 | Radcliffe et al. | |
| 6,352,002 B1 * | 3/2002 | Weijer | 73/864.74 |
| 6,405,588 B1 | 6/2002 | Hubbell et al. | |
| 6,487,920 B1 * | 12/2002 | Robbat, Jr. | 73/863.12 |
| 6,539,780 B2 | 4/2003 | Hubbell et al. | |
| 6,609,434 B2 | 8/2003 | Hubbell et al. | |
| 6,742,405 B2 | 6/2004 | Hubbell et al. | |
| 6,752,007 B1 | 6/2004 | Hubbell et al. | |
| 6,772,621 B2 | 8/2004 | Grover et al. | |
| 6,820,701 B1 | 11/2004 | Clark et al. | |
| 6,826,972 B2 | 12/2004 | Clark et al. | |
| 6,920,780 B2 | 7/2005 | Hubbell et al. | |
| 6,938,506 B2 * | 9/2005 | Henry et al. | 73/866.5 |
| 2004/0083835 A1 | 5/2004 | Casper et al. | |

OTHER PUBLICATIONS

U.S. Appl. No. 10/910,860, filed Aug. 3, 2004, entitled "Insertion Tube Methods and Apparatus.".

U.S. Appl. No. 10/973,710, filed Oct. 25, 2004, entitled "Lysimeter Apparataus.".

Applied Research Associates. Inc., Article entitled "Video Cone Penetrometer," 1999.

Applied Research Associates, Inc., Article entitled "Digital Cones," 1999, as found on the following internet address: http://www.vertek.ara.com/products/probes/video.html on Jan. 31, 2002.

Davis, Roger, et al., "Drilling method may be gold at end of rainbow for difficult terrains—option exists for drilling and collecting samples on one rig," Soil & Groundwater Cleanup, May 1997, pp. 34-36.

Environmental Protection Agency, 2001, Advanced Tensiometers for Vadose Zone Monitoring, EPA Technology Innovation Office's Tech Trends, Nov. 2001, pp. 1-5.

Gee, G.W., et al., "Hydrologic Characterization Using Vadose Zone Monitoring Tools: Status Report," PNNL-14115, Feb. 2003, 41 pages.

Hubbell, J.M., M.J. Nicholl, J.B. Sisson, and D.L. McElroy, "Application of a Darcian Approach to Estimate Liquid Flux in a Deep Vadose Zone," Vadose Zone J, vol. 3, pp. 560-570.

Hubbell, J.M. and J.B. Sisson, 1998, Advanced Tensiometer for Water Potential Measurements, Measurement and Control, October, Issue 191, p. 81-85.

Hubbell, J.M. and J.B. Sisson, 1998, "Advanced Tensiometer for Shallow or Deep Soil Water Potential Measurements," Soil Science, April, vol. 163, No. 4, pp. 271-277.

Hubbell, J.M., E.D. Mattson, J.B. Sisson, D.L. McElroy, 2002, "Water Potential in Fractured Basalt from Infiltration Events," in Evaluation and Remediation for Low permeability and Dual Porosity Environments, ASTM Special Technical Publications 1415, ed. By M.N. Sarah and L.G. Everett, ASTM International, West Conshohocken, PA, pp. 38-56.

Hubbell, J.M. and J.B. Sisson, 2003, Measuring Water Potential Using Tensiometers, Encyclopedia of Water Science, Agropedia, ed. By B.A. Stewart, Marcel Decker, Inc.—Article ID No. DOI: 10.1081/E-EWS 12000101146, pp. 904-907.

Hubbell, J.M. and J.B. Sisson, 2004, Comments on "Tensiometer modification for dimishing erros due to the fluctuating inner water column," Soil Sci. Soc. Am J., 68:709-710.

Hubbell, J.M., et al., "Understanding Fluid and Contaminant Movement in the Unsaturated Zone Using the INEEL Vadose Zone Monitoring System," 13 pages.

Hubbell, J.M., et al., "Portable Tensiometer Use in Deep Boreholes," 7 pages.

INEEL Researh and Development, "GEOPS, Geologic and Environmental Probe System," 2 pages.

McElroy, D.L. and J.M. Hubbell, "Evaluation of the Conceptual Flow Model for a Deep Vadose Zone System Using Advanced Tensiometers," Vadose Zone J., vol. 3., Feb. 2004, pp. 170-182.

McElroy, D.L., et al., "Advanced Tensiometer Monitoring Results from the Deep Vadose Zone at the Radioactive Waste Management Complex," Fiscal Year 2003, OU 7-13/14, ICP/EXT-04-00241, Mar. 2004, 28 pages.

Sisson, J.B., and J.M. Hubbell, "Water Potential to Depths of 30 Meters in Fractured Basalt and Sedimentary Interbeds," in Proceedings of the International Workshop on Characterization and Measurement of Hydraulic Properties of Unsaturated Porous Media, ed. by M.Th. Van Genuchten, et al., Salinity Laboratory, Riverside, California, 1999, pp. 855-865.

Sisson, J.B., A.L. Schafer, and J.M. Hubbell, 2000, "Vadose Zone Monitoring System for Site Characterization and Transport Modeling," in Scientific Basis for Nuclear Waste management XXIII, ed. By Robert W. Smith and David W. Shoesmith, Material Research Society, Symposium Proceedings vol. 608, Warrendale, Penn., pp. 161-166.

Sisson, J.B., et al., "Advances in Tensiometery for Long-Term Monitoring of Soil Water Pressures," Vadose Zone J., vol. 1, Nov. 2002, pp. 310-315.

U.S. Dept. of Energy, Advanced Tensiometer for Vadose Zone Monitoring, Innovative Technology Summary Report, Office of Environmental Management, Office of Science and Technology, Characterization, Monitoring and Sensor Technology Grosscutting Program and Subsurface Contaminants Focus Area, DOE/EM-0639, OST/TMS ID 2122, Sep. 2002, 40 pages.

Wisconsin Dept. of Natural Resources, Groundwater Sampling Desk Reference, PUBL-DG-037 96, Sep. 1996.

Young, Michael H., et al., The Soil Solution Phase, pp. 575-607.

Brye et al., "An Equilibrium Tension Lysimeter for Measuring Drainage through Soil," Journal of the Soil Science Society of America, 63:536-543, 1999.

"Long Term Stewardshop Technology Analysis of the Office of Science and Technology Profile," INEEL, 2001, pp. 1-235.

Szeles, C. et al., "Positron Annihilation Spectroscopy," Encyclopedia of Applied Physics, vol. 14, pp. 607-623, 1996.

Wood et al., Deficiencies in Vadose Zone Understanding at the Idaho National Engineering and Environmental Laboratory, Aug. 2000, Idaho National Engineering and Environmental Laboratory, Idaho Falls, Idaho.

* cited by examiner

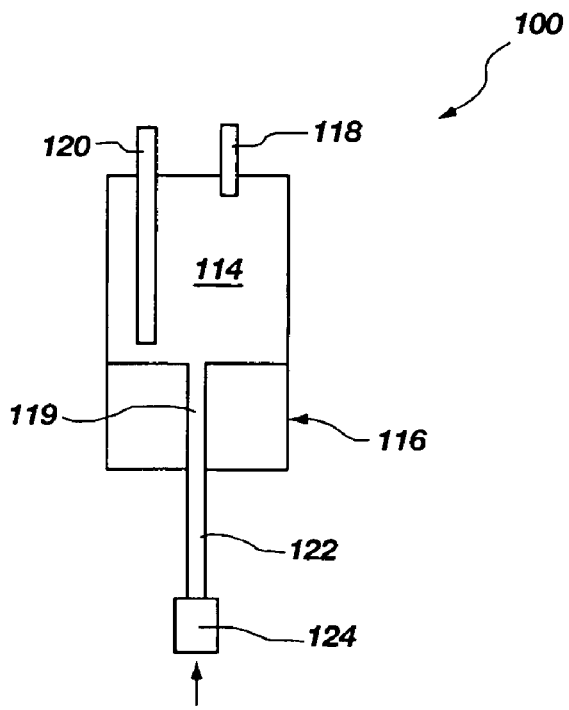
FIG. 5B-1
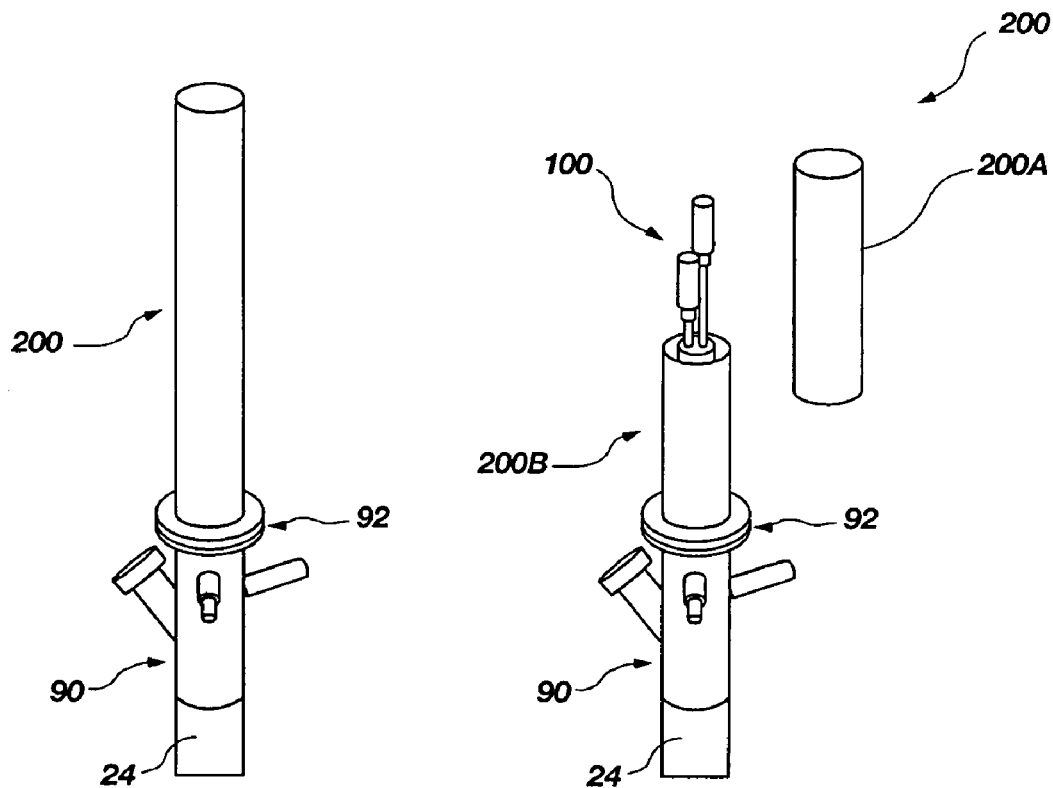
FIG. 5C  FIG. 5D

APPARATUSES FOR INTERACTION WITH A SUBTERRANEAN FORMATION, AND METHODS OF USE THEREOF

RELATED APPLICATIONS

This application is a continuation-in-part of U.S. application Ser. No. 10/376,153, filed Feb. 28, 2003, now U.S. Pat. No. 6,920,780, issued Jul. 26, 2005, entitled TENSIOMETER, DRIVE PROBE FOR USE WITH ENVIRONMENTAL TESTING EQUIPMENT, AND METHODS OF INSERTING ENVIRONMENTAL TESTING EQUIPMENT INTO A SAMPLE, the disclosure of which is incorporated by reference herein in its entirety. This application is also a continuation-in-part of U.S. application Ser. No. 10/910,860, filed Oct. 31, 2002 (now abandoned), entitled INSERTION TUBE METHODS AND APPARATUS, which is a divisional of U.S. application Ser. No. 10/285,786, filed Oct. 31, 2002 (now abandoned), entitled INSERTION TUBE METHODS AND APPARATUS, the disclosure of each of which is incorporated by reference herein in its entirety. Further, this application is a continuation-in-part of U.S. application Ser. No. 10/973,710, filed Oct. 25, 2004, now U.S. Pat. No. 6,938,503, issued Sep. 6, 2005, entitled LYSIMETER APPARATUS which is a divisional of application Ser. No. 10/285,798, filed Oct. 31, 2002, now U.S. Pat. No. 6,826,972, issued Dec. 7, 2004, entitled LYSIMETER METHODS AND APPARATUS, the disclosure of which is incorporated by reference herein in its entirety. Additionally, this application is a continuation-in-part of U.S. application Ser. No. 10/873,975, filed Jun. 22, 2004, now U.S. Pat. No. 6,976,386, issued Dec. 20, 2005, entitled TENSIOMETER METHODS, which is a divisional of U.S. application Ser. No. 10/286,709, filed Oct. 31, 2002, now U.S. Pat. No. 6,772,621, issued Aug. 10, 2004, entitled TENSIOMETER METHODS AND APPARATUS, the disclosure of each of which is incorporated by reference herein in its entirety. Also, this application is a continuation-in-part of U.S. application Ser. No. 10/285,835, filed Nov. 1, 2002, now U.S. Pat. No. 6,820,701, issued Nov. 23, 2004, entitled VISUAL PROBES AND METHODS FOR PLACING VISUAL PROBES INTO SUBSURFACE AREAS, the disclosure of which is incorporated by reference herein in its entirety.

GOVERNMENT RIGHTS

The United States Government has rights in the following invention pursuant to Contract No. DE-AC07-99ID13727 between the U.S. Department of Energy and Bechtel BWXT Idaho, LLC.

FIELD OF THE INVENTION

The present invention relates to methods and apparatus for interaction with a region of a subterranean formation. For instance, the present invention relates to methods and apparatus for sampling, indicating, or determining at least one characteristic of a region of a subterranean formation.

BACKGROUND OF THE INVENTION

Characteristics of a subterranean formation are important in many fields. Seismic properties, hydrogeologic properties, and constituents found within a subterranean formation may be of interest for a number of useful pursuits.

For instance, water and associated contaminants may seep into the ground and travel through a subterranean region known as the vadose zone (a region of unsaturated soil). Water and associated contaminant movement within the vadose zone may influence, to a large degree, a quantity of contamination (such as gasoline additives, agricultural chemicals, or buried waste leakage) that may be distributed in a water supply (such as an aquifer). Therefore, gaining an understanding of how the water and associated contaminants move in the vadose zone may be valuable for waste containment efforts. Moreover, understanding how fluids travel through a soil region may be an important aspect of environmental studies and may be helpful in developing improved irrigation. Information regarding the movement of water and associated contaminants in a vadose zone is generally acquired through the use of conventional subterranean probes or other devices.

For instance, several conventional apparatuses and methods have been used to facilitate such testing and information gathering. More specifically, conventionally, devices such as tensiometers and vapor samplers have been employed for indicating a subterranean characteristic, respectively. Further, with regard to sampling subterranean liquids, various methods and apparatus have been employed, including extraction of a soil core, introduction of vacuum-based or absorptive devices or materials, use of suction lysimeters, solution samplers, and other methods. Although there are several types of lysimeters, the term "lysimeter," as used herein refers to a device for sampling subterranean liquids, without limitation. Other conventional apparatus may involve testing soil moisture or other parameters.

Another problem associated with conventional hydrogeological sensors may be fragility. Often, conventional hydrogeological sensors are made of ceramic, tin, copper, plastics, or similar such materials and cannot be installed directly through difficult materials such as hardened soils, concrete, steel, other metals, or waste products. Further, even if a conventional hydrogeological sensor is successfully placed within a subterranean region, it may not easily be repaired or replaced.

Also, placing conventional probes into a contaminated subterranean formation for data collection may not be desirable, because the placing of conventional probes may often require drilling or coring which would bring contaminated "cuttings" to the surface and may also allow contaminated emissions to escape from the hole which is drilled. As a result, in one approach, conventional test probes may typically be placed in areas distal or peripheral to contaminated sites. Unfortunately, such probe placement only provides information when a contaminant has migrated outside of the waste disposal site area. As a further disadvantage, when a contaminant has migrated outside of the waste disposal site area, it is likely that a major contaminant plume may already exist, thus making potential remediation and containment efforts more difficult and costly.

Thus, some conventional apparatuses have been developed for addressing the above-mentioned difficulties. For example, U.S. Pat. No. 5,915,476 to Hubbell, assigned to the assignee of the present invention and the disclosure of which is incorporated, in its entirety, by reference herein, discloses a monitoring well including a conduit having a coupler which allows for assembly of a number of different monitoring devices within the monitoring well. However, a borehole must be drilled for disposing the conduit therein.

U.S. Pat. No. 6,826,972 to Clark, assigned to the assignee of the present invention and the disclosure of which is incorporated, in its entirety, by reference herein, discloses a suction lysimeter for sampling subterranean liquids wherein the casing may be driven (e.g., by direct push, sonic drilling, etc.) into a subterranean formation. However, the function of the apparatus disclosed by U.S. Pat. No. 6,826,972 to Clark is limited to a lysimeter.

In view of the foregoing, it would be highly desirable to provide improved methods and apparatuses which facilitate subterranean interaction, testing, or sampling in either contaminated or non-contaminated subterranean regions, while substantially avoiding these and other shortcomings of conventional apparatuses and methods.

BRIEF SUMMARY OF THE INVENTION

The present invention relates to methods and devices for subterranean interaction. For instance, the present invention relates to methods and apparatus for sampling, indicating, or determining at least one characteristic of a region of a subterranean formation.

More particularly, an access casing assembly for providing access to a subterranean region may comprise a casing portion comprising a plurality of casing sections operably coupled to form a central elongated cavity. Further, the access casing assembly may include a tip portion affixed to an end of the casing portion and including a porous filter through which liquid or gas may communicate with the central elongated cavity. Also, a receiving member may form a portion of the central elongated cavity and may be positioned proximate the tip portion, wherein the receiving member includes an engagement feature configured for selectively and lockingly engaging a locking structure of a device to be positioned within the access casing assembly. The access casing assembly may be structured for placement at least partially within a subterranean formation by forcing the access casing assembly thereinto.

Such a configuration may allow for a variety of selected devices to be selectively lockingly coupled to the access casing assembly, operated, and removed therefrom. Accordingly, the present invention may provide relative flexibility for interaction with a subterranean formation. Some examples of a device that may be coupled to an access casing assembly of the present invention include: a lysimeter, a tensiometer, vapor sampling device, geophysical sondes, an advective vapor sampling device, or a psychrometer, without limitation.

In another aspect of the present invention, a method of interaction with a subterranean formation may include providing an access casing assembly. The access casing assembly may comprise: a casing assembly having a casing portion comprising a plurality of casing sections operably coupled to form a central elongated cavity; a tip portion assembled to an end of the casing portion, the tip portion including a porous filter; and a receiving member positioned proximate the tip portion, wherein the receiving member includes an engagement feature configured for selectively and lockingly engaging a locking structure of a device positioned within the access casing assembly. Further, the casing assembly may be placed at least partially into a subterranean formation and the device may be placed within the casing assembly and the device and the receiving member may be selectively lockingly engaged. Also, the device may be operated for interacting with the subterranean formation.

The present invention also relates to a tensiometer. Particularly, a tensiometer according to the present invention may comprise a chamber structured for allowing at least partially filling with a fluid subsequent to contact therewith and a pressure transducer in communication with the chamber. Also, the chamber may be configured in fluid communication with a porous filter which is in fluid communication with a subterranean formation.

Additionally, the present invention also relates to a method of interaction with a subterranean formation. An access casing assembly may be provided, including a casing assembly having a casing portion comprising a plurality of casing sections operably coupled so as to form a central elongated cavity. Also, a tip portion may be assembled to an end of the casing portion, the tip portion including a porous filter. Further, a receiving member may be positioned proximate the tip portion, wherein the receiving member includes an engagement feature configured for selectively and lockingly engaging a locking structure of a device positioned within the access casing assembly. Additionally, at least one engagement hub forming a portion of the central elongated cavity and including another engagement feature configured for selectively and lockingly engaging another locking structure of the device positioned within the access casing assembly may be provided. The access casing assembly may be placed at least partially into a subterranean formation and the device may be placed within the access casing assembly including the locking structure and the at least another locking structure and selectively engaging the at least one of the engagement feature and the another engagement feature, respectively. Interaction with the subterranean formation may be achieved by operating the device.

Features from any of the embodiments described herein may be used in combination with one another in accordance with the present invention. In addition, other features and advantages of the present invention will become apparent to those of ordinary skill in the art through consideration of the ensuing description, the accompanying drawings, and the appended claims.

BRIEF DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

FIG. 3B-2 shows a perspective view of an alternative embodiment of an assembled casing tip as shown in FIG. 3A;

FIG. 3B-3 shows a perspective view of another alternative embodiment of an assembled casing tip as shown in FIG. 3A;

FIG. 5B-1 shows a schematic representation of the lysimeter shown in FIGS. 4A-4C;

FIG. 5C shows a partial perspective view of a protective cap assembled with a port tube of an access casing assembly of the present invention;

FIG. 5D shows a partial perspective view of another embodiment of a protective cap assembled with a port tube of an access casing assembly of the present invention;

DETAILED DESCRIPTION OF THE INVENTION

The present invention relates to methods and apparatuses for interaction with a region of a subterranean formation. For instance, the present invention relates to methods and apparatuses for measuring at least one characteristic of a region of a subterranean formation. Also, the present invention relates to methods and apparatus wherein an access casing assembly may be structured for selectively receiving, individually, a plurality of different sampling or interaction devices, configured for sampling or interaction with a subterranean formation, respectively.

The present invention allows for interaction with a region of a subterranean formation, such as, for instance, sampling or measuring thereof without the need for drilling, coring, or prior excavation. One method of the present invention includes placing an access casing assembly at least partially into a subterranean formation using direct push, sonic drilling, rotation, or a combination thereof and then selectively lockingly engaging a desired device thereto. Further, several different types of devices may each be selectively installed, operated, and removed from the access casing assembly. Such a configuration may allow for ease of use and may avoid drilling or driving a separate borehole for providing different device types or functions.

Figures 1A, 1B:
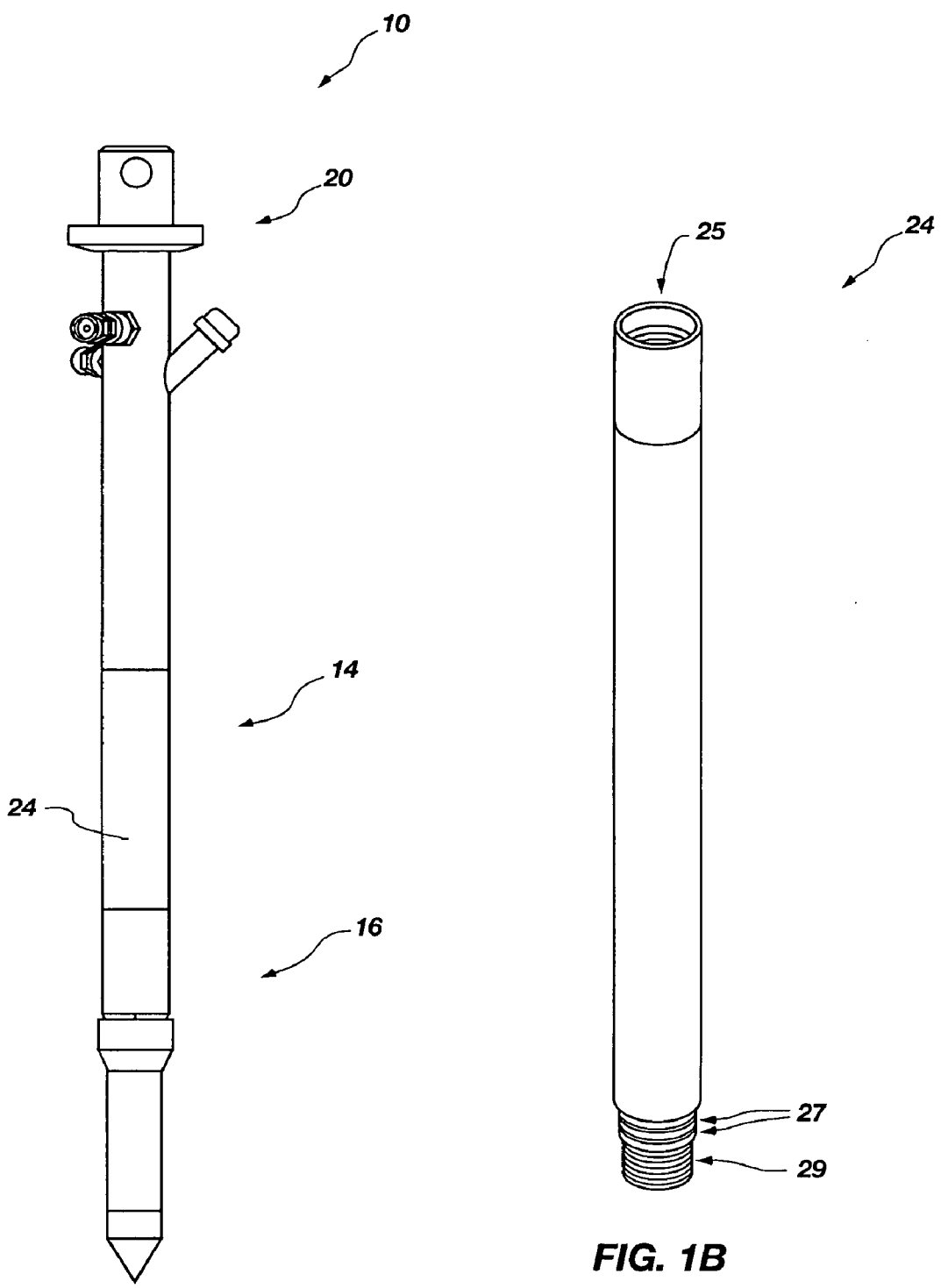
FIG. 1A shows a side view of an access casing assembly of the present invention.
FIG. 1B shows a perspective view of a casing section according to the present invention.

FIG. 1A shows a side view of an access casing assembly 10 of the present invention for providing access to a region of a subterranean formation. The access casing assembly 10, as shown in FIG. 1A comprises a casing tip 16, a casing portion 14, and, optionally, a ported casing cap 20. Each of the casing tip 16, casing portion 14, and ported casing cap 20 may be affixed to one another and, preferably, sealed to one another at respective connection joints, as by welding or other joining configuration as known in the art, so as to inhibit gas or fluid from entering or exiting through the connection joints. Such a configuration may form a central elongated cavity within the access casing assembly 10.

Turning to the components of access casing assembly 10, casing sections 24 may be releasably engaged with one another, as by threaded connections or may be coupled or secured to one another by welding or as otherwise known in the art. A perspective view of a casing section 24 is shown in FIG. 1B, including an upper connection end 25, lower connection end 29, and sealing features 27. Preferably, casing sections 24 may be coupled to one another so as to form a hermetic seal, thus preventing gas or liquid from escaping from the interior of the casing portion 14. Accordingly, at least one sealing element (not shown) may be positioned between adjacent casing sections 24 so as to provide a seal therebetween. For instance, sealing features 27 of lower connection end 29 may comprise a groove for disposing an O-ring therein, so as to seal against a surface of an adjacent casing section 24 when assembled therewith. Also, upper connection end 25 may include a threaded bore as well as a surface against which sealing features 27 of a lower connection end 29 of an adjacent casing section 24 may sealingly engage. Thus, assembled casing sections 24 may be structured for inhibiting gas or liquid communication through their connecting joint.

Figure 1C:
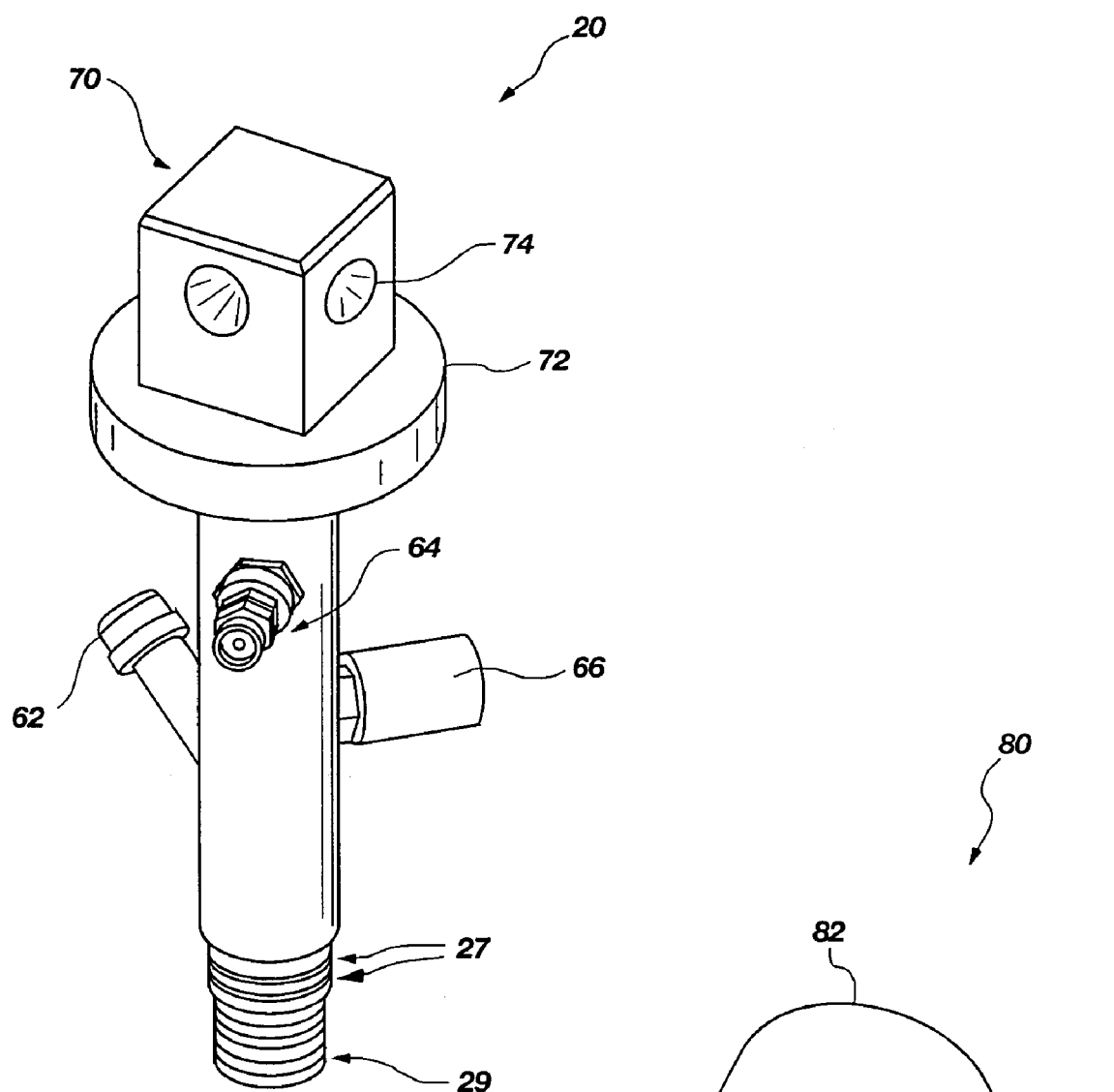
FIG. 1C shows a perspective view of an embodiment of a casing cap according to the present invention.
Figure 1D:
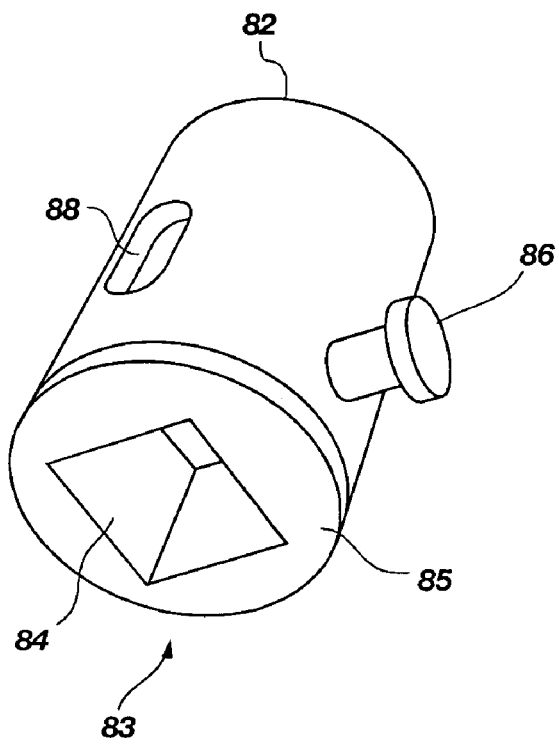
FIG. 1D shows a perspective view of a drive shoe according to the present invention.
Figure 1E:
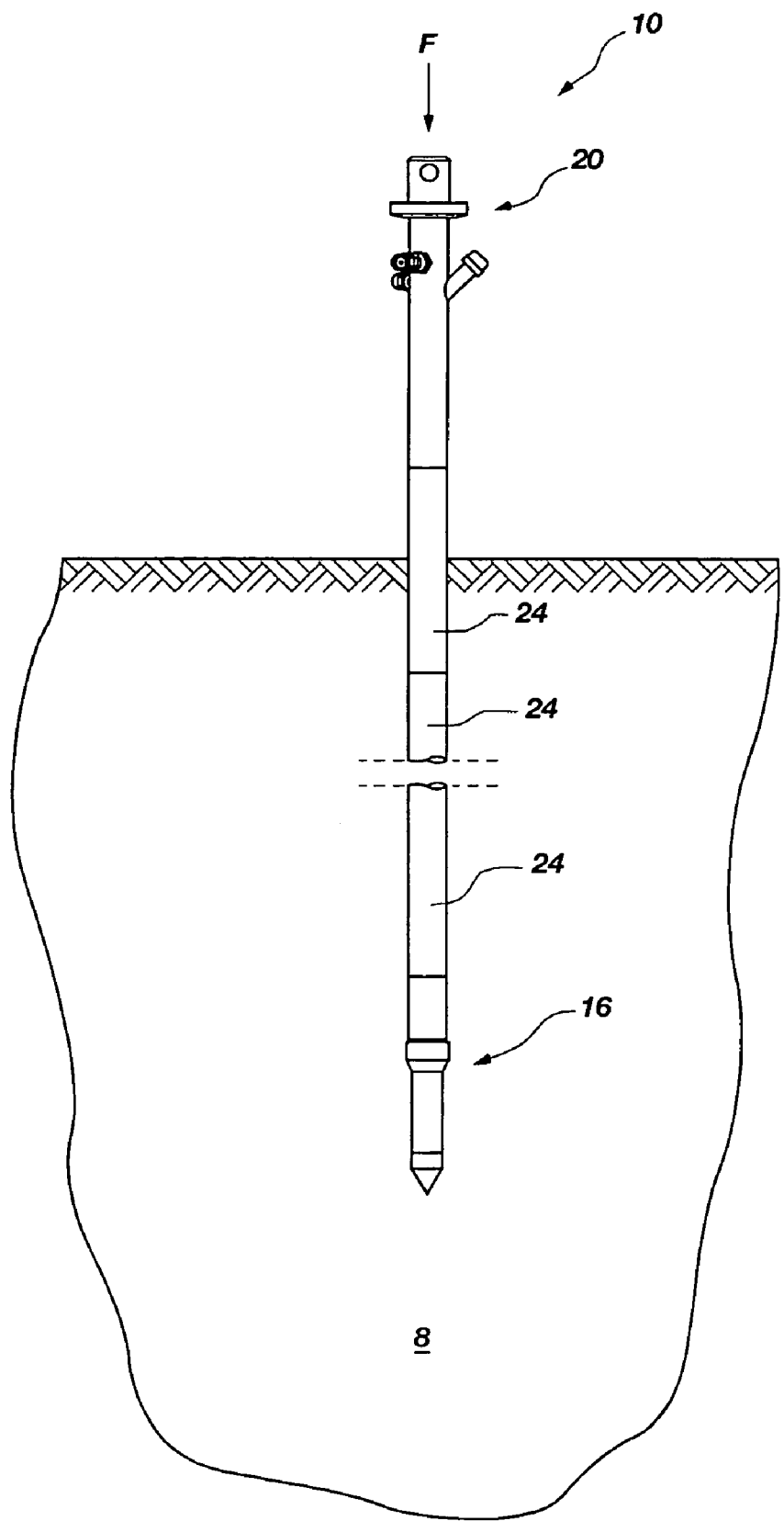
FIG. 1E shows a side schematic view of an embodiment of an access casing assembly of the present invention positioned partially within a subterranean formation.

Such a configuration may prevent leakage of hazardous materials from escaping the access casing assembly 10 after it is at least partially disposed within a subterranean formation 8, as shown in FIG. 1E. Thus, the access casing assembly 10 may be configured with a sealing system that prohibits potential contamination from emitting from the surrounding subterranean formation into the access casing assembly 10 and to the surface of the subterranean formation. Further, the access casing assembly 10 may include a seal system that provides a contamination barrier between the surrounding medium and the central elongated cavity (and the subterranean formation surface). The seal system feature may further provide contamination confinement during ground installation and during instrument insertion, operation, and eventual retrieval. Of course, an access casing assembly 10 may be useful for use within subterranean formations where providing a contamination barrier is not required or may be less critical. Thus, the sealing structure, system, or configuration may be tailored according to the demands of the environment in which it is to be placed.

The casing portion 14 of access casing assembly 10 may include at least one casing section 24 or, alternatively, a plurality of casing sections 24, which are assembled to one another. Casing sections 24 may each comprise a metal, such as, for instance, stainless steel, carbon steel, aluminum, or another suitable material, and may include at least a substantially transparent portion, for allowing visual inspection of the subterranean formation. U.S. Pat. No. 6,820,701 to Clark, assigned to the assignee of the present invention and the disclosure of which is incorporated in its entirety by reference herein, discloses a visual probe for use within subterranean formations.

In further detail, each of casing sections 24 may comprise a material having a suitable wall thickness and strength to withstand the forces associated with placement of the access casing assembly 10 at least partially into a subterranean formation, as discussed hereinbelow. Accordingly, it may be preferable to configure access casing assembly 10 as an elongated body with a sharpened tip, for ease in placement within a selected region of a subterranean formation.

As shown in FIG. 1C, casing cap 20 may include a lower connection end 29 for threaded or other affixation to casing portion 14 of access casing assembly 10 and casing cap 20 may include a drilling engagement end 70, sized and configured for assembly with a drive apparatus, such as a drill rig or other equipment for providing impetus for placement of access casing assembly 10 at least partially within a subterranean formation. Casing cap 20 may further include a lower connection end 29 and sealing features 27 configured for attachment and sealing to upper connection end 25 of a casing section 24. Accordingly, at least one sealing element (not shown) may be positioned between the casing cap 20 and a casing section 24 affixed thereto so as to provide a seal therebetween. For instance, sealing features 27 of lower connection end 29 may comprise a groove for disposing an O-ring within, so as to seal against or with a surface of an adjacent casing section 24 when assembled therewith.

Casing cap 20 may also include an abandonment port 62, a gas port 64, and a fluid port 66, wherein each port 62, 64, and 66 is communicative with an interior of the tubular body of the casing cap 20. Gas port 64 may be configured for introducing a gas into access casing assembly 10 or expelling a gas therefrom. Similarly, fluid port 66 may be configured for introducing a fluid into access casing assembly 10 or expelling a fluid therefrom. Fluid port 66 may comprise a quick-disconnect type hydraulic fitting, or other flow controlling fitting (i.e., a valve) as known in the art. Similarly, gas port 64 may comprise a quick-disconnect type hydraulic fitting, or other hydraulic conduit as known in the art. Commercially available quick-disconnect type gas and hydraulic fittings are available from Parker Hannifin of Cleveland, Ohio or Swagelok of Solon, Ohio. Thus, the access casing assembly 10 may form a central elongated cavity wherein each port 62 and 64 (also port 66, as discussed below) may be selectively communicative therewith.

Also, abandonment port 62 may be sized and configured for introducing a filling material (i.e., sand, grout, cement, etc.) into the access casing assembly 10. Such a configuration may be desirable if it is determined that the access casing assembly 10 is not suitably sealed with respect to a subterranean formation within which it is installed. In such a situation, it may be preferable to fill the access casing assembly 10 with a filling material and install a filter (e.g., a HEPA or other filter) to the gas port to provide a protected vent for safely releasing gases therefrom.

Turning to the engagement end 70 of the casing cap 20, the drilling engagement end 70 may be structured for transferring forces associated with placement of the access casing assembly 10 into a subterranean formation. As shown in FIG. 1C, the engagement end 70 may comprise a substantially cubical shape and may include at least one retention feature 74 for accepting a locking element 86 (FIG. 1D) therein. In further detail, engagement end 70 may include a flange portion 72 for transferring longitudinal forces to the access casing assembly 10 during placement thereof at least partially within a subterranean formation. However, it should be understood that the shape of the engagement end 70 of the casing cap 20 of the present invention is not so limited; rather, the engagement end 70 may be suitably shaped so as to allow for coupling to drive shoe 80 (FIG. 1D) during placement of the access casing assembly 10 at least partially into a subterranean formation, as explained further hereinbelow. More specifically, the access casing assembly 10 may be structured for placement into and through hardened sediments and difficult debris (i.e., steel drums and other hardened materials) using conventional direct-push, sonic drilling, rotary drilling techniques, or a combination thereof to a desired depth, without bringing drill cuttings to the ground surface.

FIG. 1D shows a drive shoe 80 having a casing cap engagement end 83 and an equipment coupling end 82. The casing cap engagement end 83 of the drive shoe 80 may comprise an insert element 85 including an aperture or depression 84 formed thereinto and may be, preferably, shaped complementarily with respect to the engagement end 70 of the casing cap 20. The equipment coupling end 82 may comprise a threaded connection as known in the art, such as a tapered threaded connection (e.g., an American Petroleum Institute ("API") thread type). In addition, drive shoe 80 may include at least one locking element 86 for positioning and affixing the casing cap 20 with respect to the drive shoe 80 when assembled to one another during placement of an access casing assembly 10 within a subterranean formation. The at least one locking element 86 may comprise a threaded element, such as a bolt with an end that is sized and configured for engaging the at least one retention feature 74 of the engagement end 70 of the casing cap 20. Of course, while the at least one locking element 86 is shown in FIG. 1D as a plurality of threaded bolts, the present invention is not so limited. Rather, the at least one locking element 86 in combination with retention feature 74 may comprise at least one pin, cam, or other interlocking structure as known in the art, without limitation. For example, in an alternative embodiment, a pin may extend completely through the engagement end 70 of the casing cap 20 for affixing it to the drive shoe 80.

Optionally, drive shoe 80 may include an aperture 88 for allowing ingress and egress of cables, conduits, or other operational equipment. Of course, in such a configuration, optionally, an aperture or hole (not shown) may also be formed through the engagement end 70 of the casing cap 20 to allow for passage of such cables, conduits, or other operational equipment.

Thus, turning to FIG. 1E, generally, access casing assembly 10 may be structured for at least partial placement within a subterranean formation 8. As shown in FIG. 1E, access casing assembly 10 may include a plurality of casing sections 24 each extending at least partially into subterranean formation 8. Access casing assembly 10 may be placed at least partially within subterranean formation 8 by way of direct push, sonic drilling, rotation, a combination thereof, or as otherwise known in the art. Such a configuration may be advantageous for avoiding drilling operations in which cuttings may be generated and carried to the surface of subterranean formation 8, since, if a contaminated region of subterranean formation 8 were encountered, generation of such contaminated cuttings may be undesirable. It may be appreciated that the structure and size of access casing assembly 10 may be selected for placement of the nose portion 32 (FIGS. 3A and 3B) thereof within or proximate to a selected region of interest of subterranean formation 8. Further, the orientation of access casing assembly 10 with respect to the subterranean formation 8 may be selected, without limitation.

In one approach, the entire access casing assembly 10 may be assembled including each of the plurality of casing sections 24 prior to placement at least partially within a subterranean formation 8 and then driven or otherwise placed therein by application of a force F (FIG. 1E) to the casing cap 20. Alternatively, one or more additional casing section 24 may be assembled to access casing assembly 10 sequentially, by repeatedly driving the access casing assembly 10 farther into the subterranean formation 8, removing the casing cap 20, and assembling an additional casing section 24 to the casing portion 14.

Figure 3A:
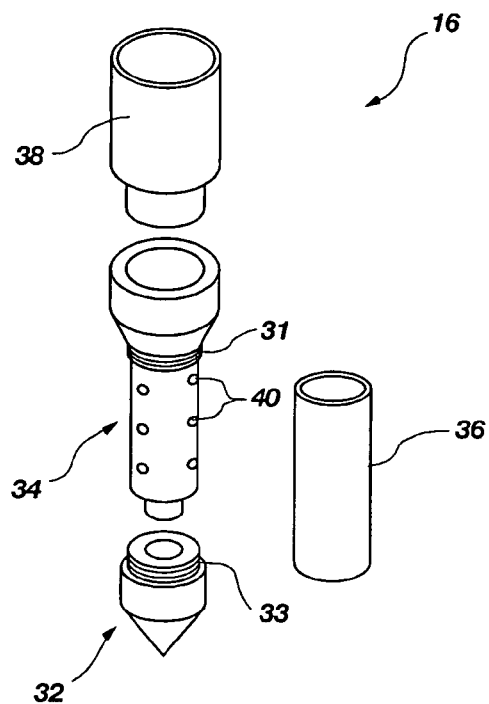
FIG. 3A shows an exploded perspective view of an embodiment of a casing tip according to the present invention.
Figures 1, 3B:
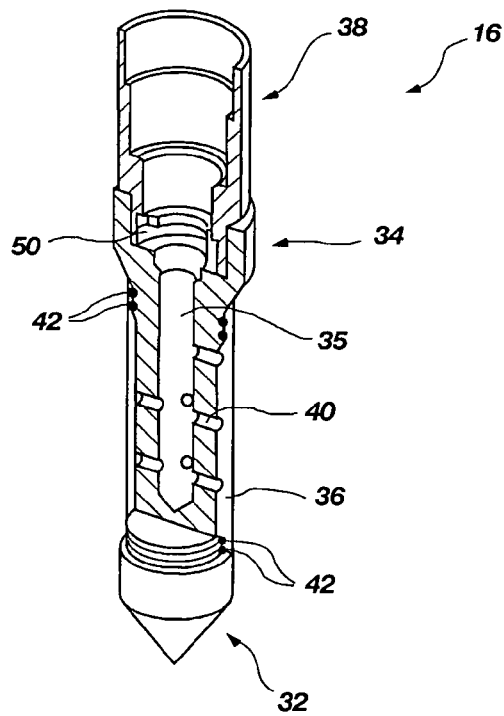
FIG. 3B-1 shows a partial cross-sectional view of an assembled casing tip as shown in FIG. 3A.

A method of installation of access casing assembly 10 at least partially within a subterranean formation 8 will be described hereinbelow, with reference to FIG. 1E. Initially, access casing assembly 10 may be assembled and affixed to equipment for driving access casing assembly 10 at least partially into a subterranean formation 8, such as a drill rig (not shown). A quantity of fluid, such as, for instance, water, may be placed into the access casing assembly 10 via the fluid port 66, and the access casing assembly 10 may be oriented so that the water resides within the bore 35 of the body 34 of the casing tip 16 (FIGS. 3A and 3B). Fluid disposed within body 34 may effectively seal the porous filter 36 (FIGS. 3A and 3B) because it may require a relatively large pressure gradient between the outer surface of the porous filter 36 and the bore 35 of the body 34 of the casing tip 16 to force the fluid therethrough. Of course, a sufficient amount of fluid may be provided in contact with porous filter 36 so that the pores thereof are substantially filled therewith (e.g., by substantially filling the bore 35 of body 34 with fluid or by partially filling bore 35 of body 34 with fluid and allowing capillary action of the porous filter 36 to substantially fill the pores thereof with the fluid). Any appropriate fluid may be employed, depending on the desired properties of the fluid and the characteristics of the porous filter. For instance, it may be desirable to select at least one property (i.e., viscosity, density, etc.) of the fluid for providing a desired behavior or function (e.g., providing a desired pressure gradient for forcing the fluid through the porous filter 36).

Once a fluid (e.g., water) is placed within the access casing assembly 10, the access casing assembly 10 may be pressure tested to verify the pressure holding integrity thereof. More specifically, gas may be introduced within the access casing assembly 10 via the gas port 64, and the pressure therein may be measured. Upon developing a certain level of pressure, it may be substantiated that the fluid or gas communication path into or from the access casing assembly 10 is substantially solely by way of (i.e., through) the porous filter 36. Alternatively, if the access casing assembly 10 is not suitably sealed with respect to the subterranean formation 8, a filling material (i.e., sand, grout, cement, etc.) may be introduced into the access casing assembly 10 via abandonment port 62 for sealing the central elongated cavity of the access casing assembly 10 to inhibit or prevent subsequent contamination from communicating therethrough.

Thus, access casing assembly 10 may be driven or placed at least partially into a subterranean formation 8 by direct push, sonic drilling, rotation, or a combination thereof, or as otherwise known in the art. During placement of the access casing assembly 10 at least partially into the subterranean formation 8, additional casing sections 24 may be installed to lengthen the access casing assembly 10. Ultimately, the length of the access casing assembly 10 may be from between about one foot at least to hundreds of feet.

Of course, repeated pressure testing may be performed and additional fluid may be introduced into the access casing assembly 10 for maintaining a sealing function in relation to the porous filter 36. Accordingly, placement of the access casing assembly 10 may proceed, with assembly of additional casing sections 24 to access casing assembly 10, if necessary, and repeated pressure testing, as desired, until the access casing assembly 10 is positioned at a selected depth within or proximate to a selected region of the subterranean formation 8. Also, it should be noted that the orientation of the access casing assembly 10 prior to placement or as it is driven into the subterranean formation 8 may be selected, altered, maintained, or modified for ultimately positioning the access casing assembly 10 in a desired position and orientation.

Figure 2A:
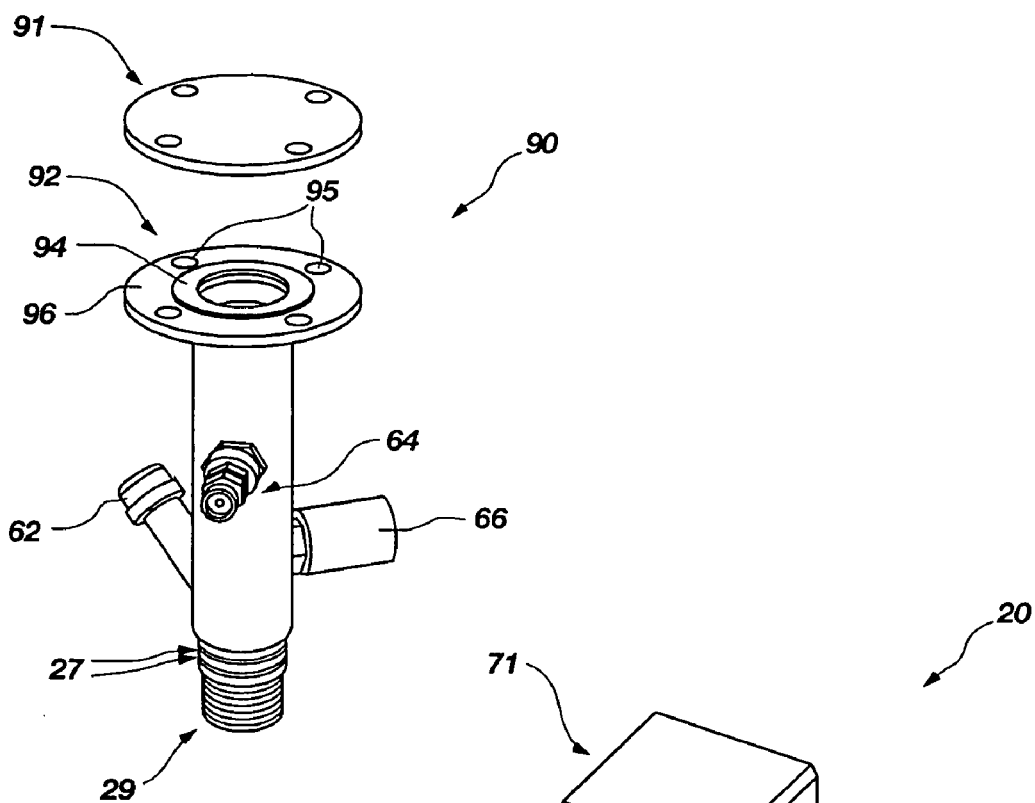
FIG. 2A shows a perspective view of an embodiment of a port tube according to the present invention.
Figure 2B:
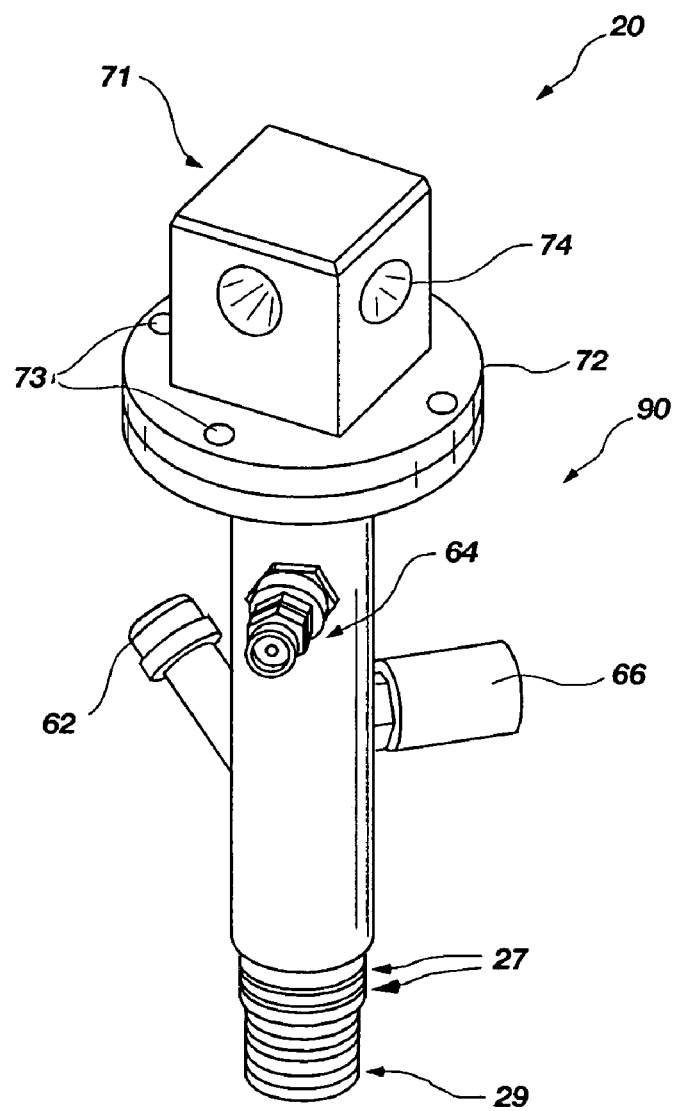
FIG. 2B shows an alternative embodiment of a casing cap according to the present invention.

Once access casing assembly 10 has been desirably placed at least partially within the subterranean formation 8 and, optionally, pressure tested, the casing cap 20 may be removed therefrom and a port tube 90, as shown in FIG. 2A may be installed thereon. Port tube 90 is shown in FIG. 2A in a perspective view and, as shown therein, is similar to the casing cap 20, but has a flanged open end 92, which may be optionally closed via cap 91, instead of the drilling engagement end 70 of the casing cap 20. In further detail, flanged open end 92 may include a radially extending flange 96 and apertures 95 for accommodation of fastening elements, such as bolts. Further, flanged open end 92 may include at least one gasket 94 for sealing against a surface (e.g., cap 91) mated thereagainst. Optionally, in an alternative embodiment shown in FIG. 2B, casing cap 20 may be formed by selectively affixing a removable equipment engagement end 71 to the flanged open end 92 of the port tube 90 by way of affixation elements 73 (e.g., bolts, pins, etc.).

The port tube 90 may allow for access into the access casing assembly 10, through flanged open end 92, for installation and removal of sampling, interaction, measurement, or observation devices therein. Generally, a device may be sized and configured for placement within the access casing assembly 10. Such a device may be advantageously configured for indication, measurement, or sampling of at least one subterranean characteristic. Also, such a device may be configured to mate or engage with engagement feature 50 (FIG. 3B) of receiving member 38 (FIGS. 3A and 3B) of casing tip 16 (FIGS. 3A and 3B).

Optionally, a device configured for placement within access casing assembly 10 may be placed within a sealable container (e.g., a plastic bag or other container) prior to use thereof and for substantially hermetically isolating the device. Of course, subsequent to use within access casing assembly 10, a device may be placed within a sealable container (e.g., a plastic bag or other container) for substantially hermetically isolating the device. Such storage of the device may preserve a level of cleanliness of the device or, alternatively, may prevent contamination from the device after use thereof.

It may be further appreciated that access casing assembly 10 may be structured for allowing retrieval of at least a portion thereof from the subterranean formation 8. In one example, it may be determined that the placement of the access casing assembly 10 may be undesirable, or the region of the subterranean formation 8 within which the access casing assembly 10 is installed may not be of interest (e.g., not contaminated, or undesirable). Thus, it may be desired to remove the access casing assembly 10 from the subterranean formation 8 after it has been placed at least partially therein. Explaining further, a longitudinally upward force may be applied to the access casing assembly 10 for removal thereof. For instance, the casing cap 20 may be affixed to the casing portion 14, affixed to a drill rig (or other pulling device), and the entire access casing assembly 10 may be pulled from the subterranean formation 8 for repair, if necessary, and reuse. Alternatively, at least a portion of the access casing assembly 10 may be severed from a remaining portion thereof and retrieved for repair, if necessary, and additional use.

Generally, the access casing assembly 10 may include at least one structure configured for interaction with a proximate region of the subterranean formation 8 within which it is positioned. In one embodiment, the casing tip 16 may be configured for fluid or gas communication with the subterranean formation 8. For instance, FIG. 3A shows an exploded, perspective view of the casing tip 16 including a nose portion 32, a body 34, a porous filter 36, and a receiving member 38. Body 34 and nose portion 32 may comprise a metal, such as, for instance, stainless steel, carbon steel, aluminum, or another suitable material as known in the art. The porous filter 36 may be positioned about the body 34 and may be assembled so as to generally surround the body 34 and positioned and configured for filtering fluids or gasses that pass through the at least one port 40 of the body 34. Thus, in such a configuration, fluid or gas communication with a central elongated cavity within the access casing assembly 10 formed by the casing tip 16, casing portion 14, and ported casing cap 20 may substantially or entirely occur through the porous filter 36.

Preferably, porous filter 36, body 34, and nose portion 32 may be sized and configured so that, upon assembly thereof, there is ample longitudinal space for porous filter 36 to be positioned without interference with body 34 or nose portion 32. For instance, there may be a 1/32 inch gap provided between the porous filter 36 and the body 34 and between the porous filter 36 and the nose portion 32. In addition, at least one sealing feature 31 may be provided and positioned proximate a first end region of the porous filter 36 between the porous filter 36 and the body 34 and at least one sealing feature 33 may be provided and positioned proximate a second end region of the porous filter 36 between the porous filter 36 and the body 34. Sealing features 31 and 33 may comprise annular grooves sized and configured for accepting a sealing element, such as an O-ring. Such a configuration may prevent liquids or gasses from passing into or from body 34 through at least one port 40 without passing through the porous filter 36.

Thus, since only the sealing elements (not shown) contact the porous filter 36, during compression of body 34 and nose portion 32, porous filter 36 may be substantially unaffected. Put another way, such a configuration may substantially inhibit forces or moments (e.g., bending, tension, compression, or shear) experienced by the body 34 or nose portion 32 from being transferred to the porous filter 36. Alternatively, the porous filter 36 may be welded, brazed, or otherwise sealed to the body 34 so that fluid or gas communication with the at least one port 40 occurs through the porous filter 36. Optionally, a sealant such as a silicone or other sealant as known in the art may be employed for sealing, affixing, or both sealing and affixing the porous filter 36 to the body 34.

Porous filter 36 may comprise at least one of a sintered metal filter (e.g., sintered steel, sintered stainless steel, sintered bronze, etc.), a charcoal filter, a mesh filter (e.g., nylon mesh), a porous ceramic filter, a membrane filter, or any other fluid or gas filter as known in the art. For example, an exemplary porous filter may be commercially available from Soil Measurement Systems of Tucson, Ariz., Mott Metallurgical Corporation of Farmington, Conn., or GKN Sinter Metals GmbH of Germany. In one embodiment, porous filter 36 may exhibit nominal pore openings of about 0.1 micron to about 10 microns.

In one aspect of the present invention, the access casing assembly 10 may be structured for selective engagement and assembly with a device positioned within the central cavity of the access casing assembly 10. Generally, the access casing assembly 10 may include at least one stabilizing or engagement feature for positively securing a device therein. For instance, the receiving member 38 may be structured for selective and releasable assembly with a locking structure of a device or instrument, as described in more detail hereinbelow.

In one embodiment, as shown in FIG. 3B-1, the receiving member 38 may be configured with at least one engagement feature 50, structured for accepting a suitably structured locking structure of an instrument or device. Of course, any number of selective, releasable, or temporary fastening configurations may be employed, as known in the art. For instance, one exemplary type of selective, temporary mechanical affixation configuration may include a so-called bayonet-type mounting, wherein a pair of mating connector halves may be releasably mated and disassembled by way of respective interlocking pins and grooves or slots, which are rotated with respect to one another, usually less than one full revolution.

Figures 2, 3B:
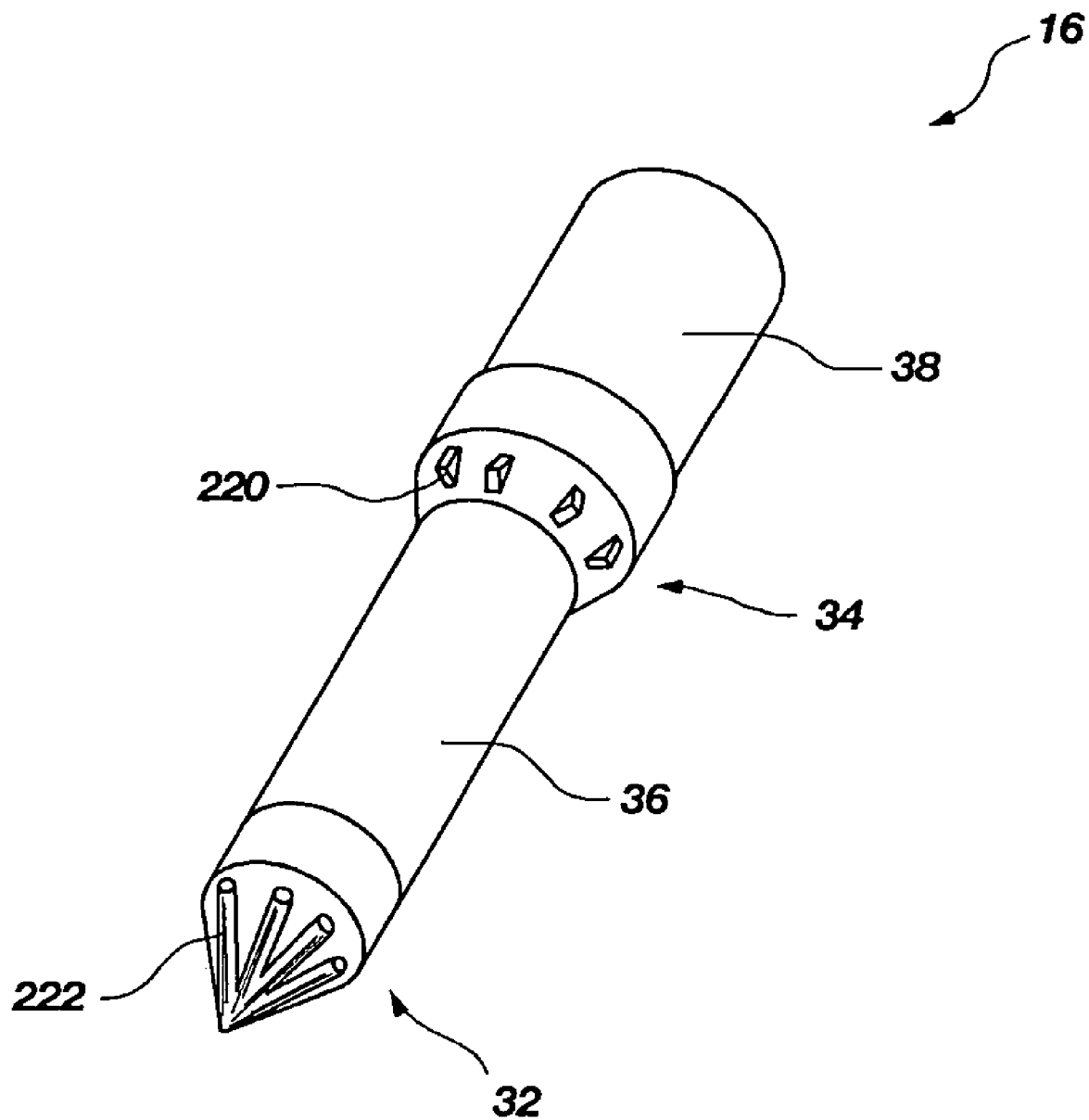

In another embodiment, at least one of the nose portion 32, body 34, and receiving member 38 may be structured with recesses or protrusions for facilitating placement of the access casing assembly 10 within a subterranean formation. For example, FIG. 3B-2 shows a casing tip wherein body 34 and nose 32 include protrusions 220 and 222. Protrusions 220 and 22 may comprise welded beads or blades that extend from body 34 and nose 32, respectively. In one embodiment protrusions 220 and 22 may be configured for resisting wear. Particularly, protrusions 220 and 22 may comprise a so-called hardfacing material, or other wear resistant material as known in the art. As known in the art hardfacing materials may include materials (e.g., tungsten carbide) deposited by way of flame-spraying, welding, via laser beam heating, or as otherwise known in the art.

Figures 3, 3B:
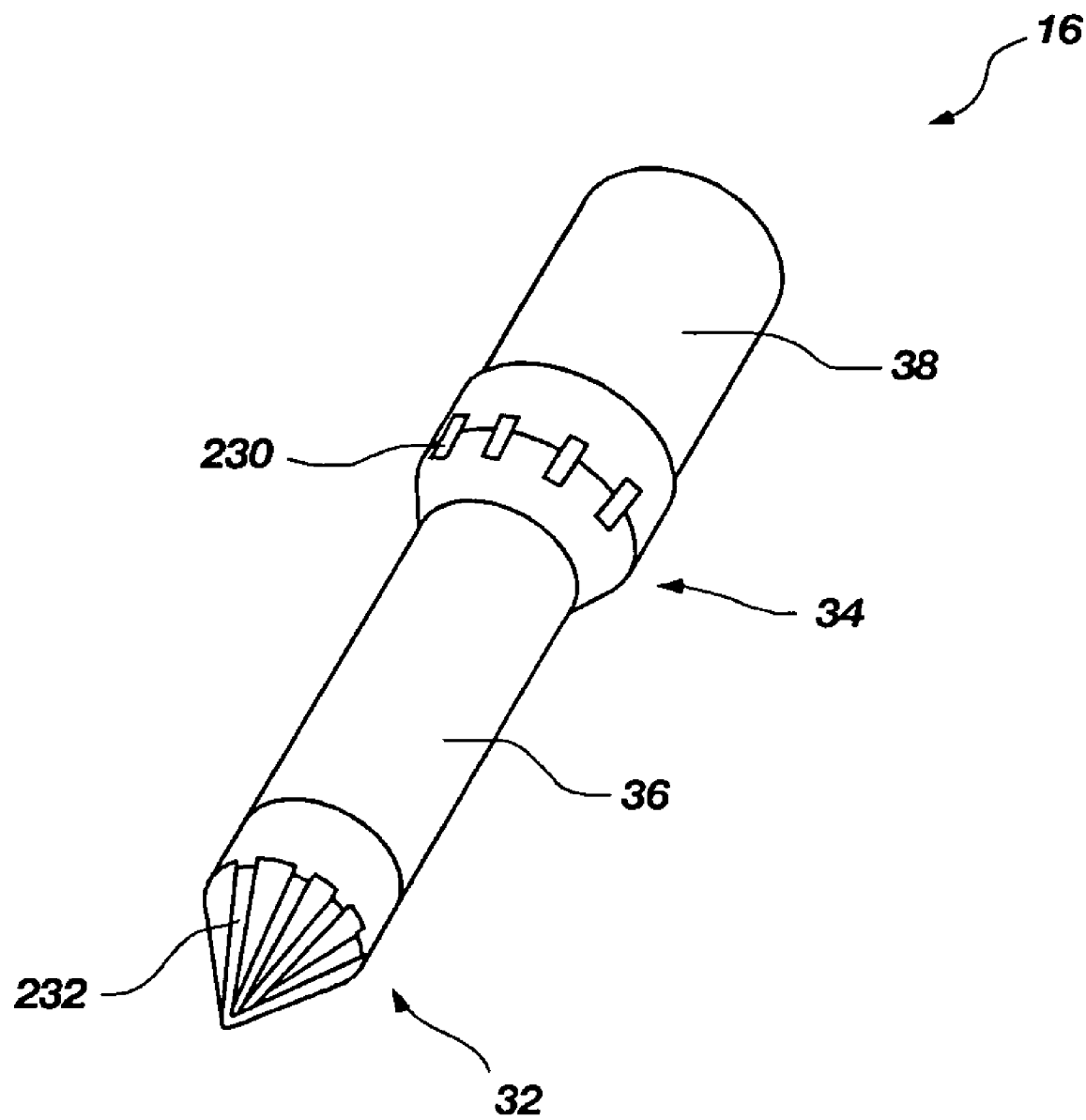
Figure 3C:
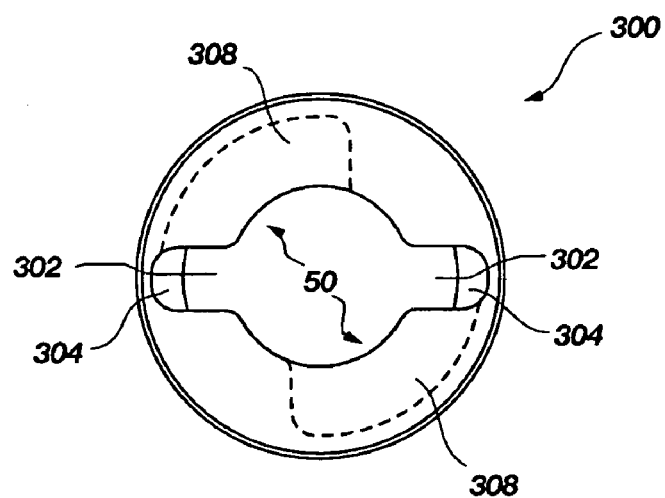
FIG. 3C shows a top elevation view of an embodiment of a receiving hub according to the present invention.

Alternatively, as shown in FIG. 3B-3, grooves or recesses 230 and 232 may be formed within body 34 and nose 32, respectively. Such a configuration may facilitate placement of an access casing assembly 10 within a subterranean formation by creating cutting edges upon the casing tip 16, which may be particularly useful if casing tip 16 is rotated.

Figure 3D:
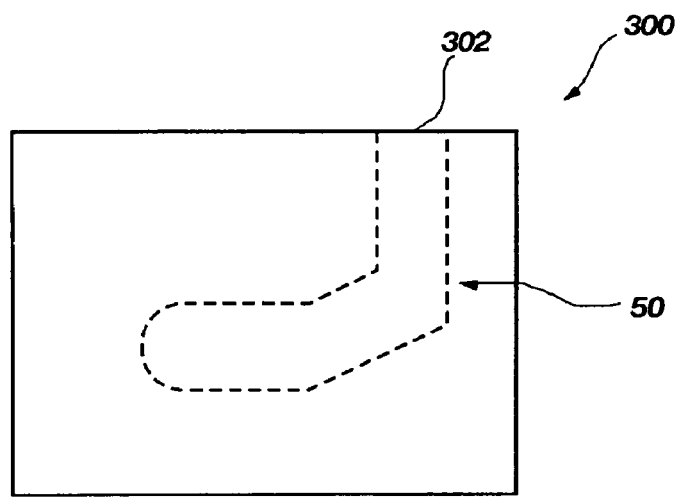
FIG. 3D shows a side schematic view of an embodiment of a groove formed in a receiving hub receiving hub shown in FIG. 3C.
Figure 3E:
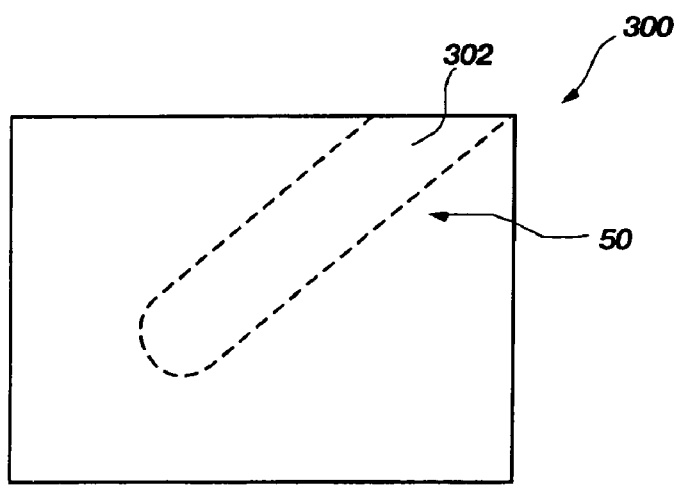
FIG. 3E shows a side schematic view of another embodiment of a groove formed in a receiving hub shown in FIG. 3C.
Figure 3F:
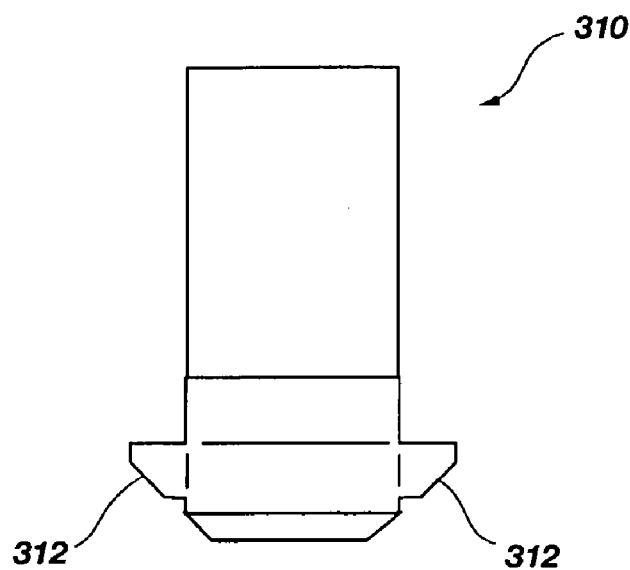
FIG. 3F shows a side view of an embodiment of a locking structure according to the present invention.

In further detail, FIGS. 3C-3F show a bayonet-type connection configuration, wherein a receiving hub 300 includes two engagement features 50 comprising grooves 308 which partially circumferentially extend along an interior of the receiving hub 300. Also, an exemplary locking structure 310 is shown in FIG. 3F, in a side view, including radially extending elements 312. Radially extending elements 312 may be of a generally rounded cross section, a generally rectangular cross section, or a generally square cross section and sized and configured for movement within grooves 308. Landing surfaces 304 of receiving hub 300 may be formed substantially transverse to keyways 302, so that radially extending elements 312 of locking structure 310 may enter keyways 302 and mate against landing surfaces 304, respectively. Then, rotation of locking structure 310 may move radially extending elements 312 into respective grooves 308. It should be appreciated that grooves 308 may also extend longitudinally, as shown in FIGS. 3D and 3E, showing partial schematic side views of grooves 308 formed in receiving hub 300.

In one embodiment of the present invention, it may be advantageous to position a receiving member 38 including an engagement feature 50 positioned proximate the porous filter 36 of casing tip 16. Such a configuration may allow for ease in interaction with a region of a subterranean formation through the porous filter 36. Thus, as shown in FIG. 3B, showing a cross-sectional view of casing tip 16, the body 34 may be affixed to the nose portion 32 and the receiving member 38 may be affixed to the body 34. For example, each of the body 34, nose portion 32, and the receiving member 38 may be threaded to one another, welded to one another, or otherwise affixed to one another as known in the art. The body 34 may include a cavity or bore 35 extending therein and in communication with at least one port 40 extending from an outer surface thereof. Further, the porous filter 36 may be assembled about the body 34 and sealing elements 42 (e.g., O-rings) may be positioned between the porous filter 36 and the body 34 so that gas or fluid passing to or from the at least one port 40 of the body 34 also passes through the porous filter 36.

Figure 4A:
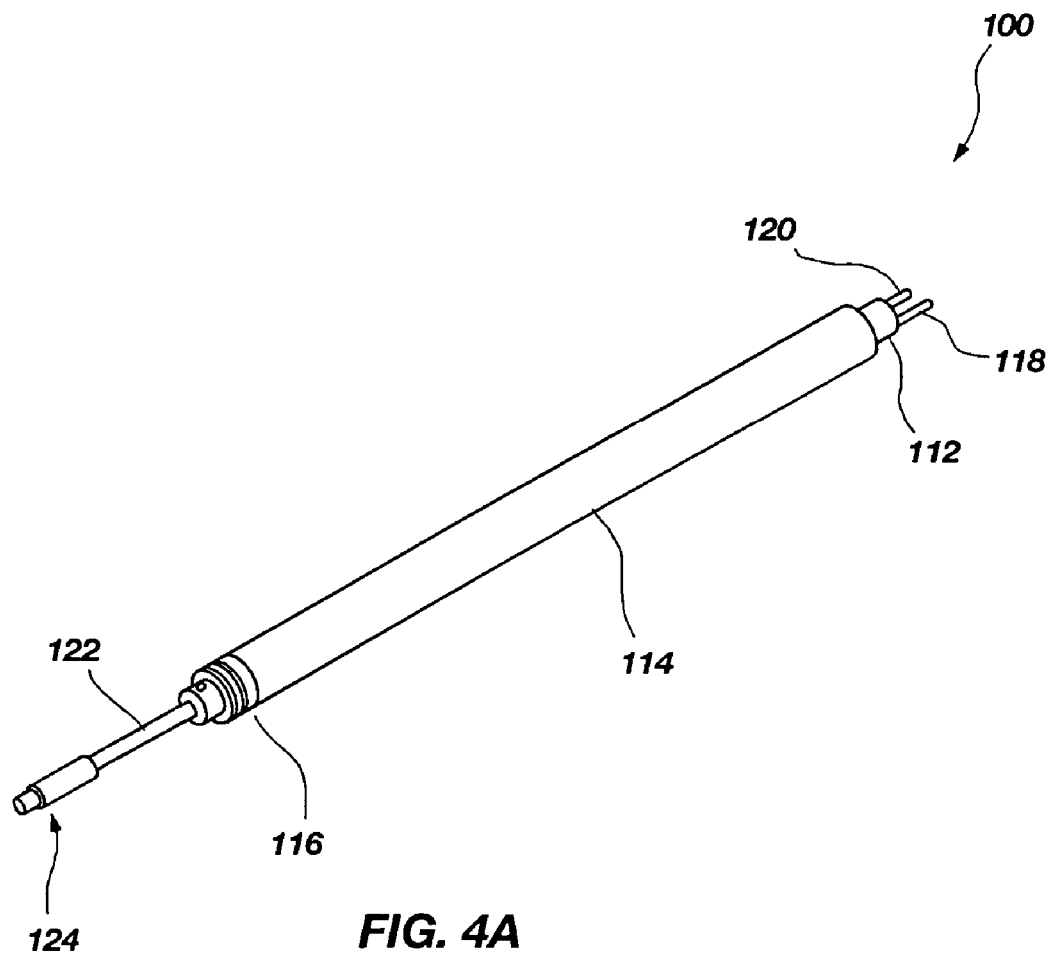
FIG. 4A shows a perspective view of a lysimeter according to the present invention.
Figure 4B:
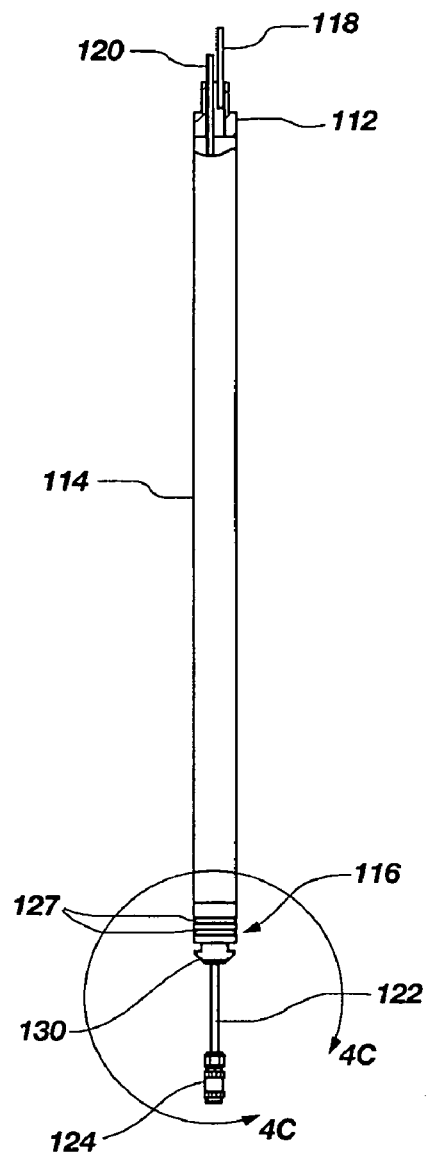
FIG. 4B shows a side view of the lysimeter shown in FIG. 4A.
Figure 4C:
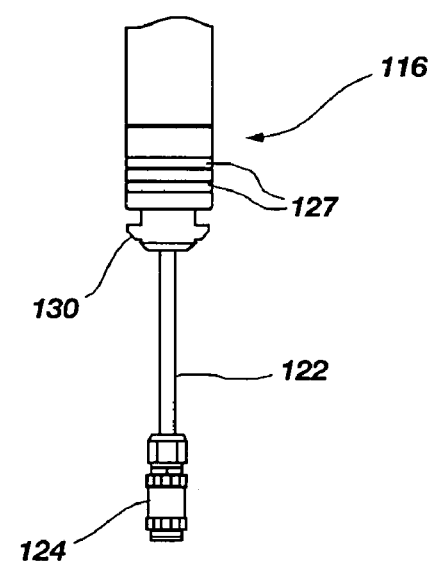
FIG. 4C shows a partial, enlarged side view of a lower end of the lysimeter shown in FIG. 4B.

For instance, one device which may be installed within access casing assembly 10 for sampling of subterranean liquids is a lysimeter apparatus. As shown in FIGS. 4A-4C in a perspective view, a side view, and an enlarged partial side view, respectively, a lysimeter 100 may be provided, comprising a top plug 112, a reservoir portion 114, and a bottom plug 116. The top plug 112 and bottom plug 116 may be installed within the reservoir portion 114. In addition, a sample tube 120 may extend from proximate the bottom plug 116 through the reservoir portion 114 and through the top plug 112. Also, a vacuum/pressure tube 118 may extend through the top plug 112 and may communicate with the reservoir portion 114. Further, a draw tube 122 and a check valve 124 may be assembled to the bottom plug 116 and may be configured for allowing drawing a sample of a fluid or gas from the bore 35 of body 34 therethrough, as described hereinbelow.

Lysimeter 100 may be placed within the access casing assembly 10, the bottom plug 116 including a locking structure 130 for engaging the engagement feature 50 of receiving member 38 of the casing tip 16. In addition, bottom plug 116 may include at least one sealing feature 127, such as a groove for accepting a sealing element, such as an O-ring, for sealing against the receiving member 38 of the casing tip 16. Alternatively, the receiving member 38 may include at least one sealing feature 127, such as a groove for accepting a sealing element, such as an O-ring for sealing against the bottom plug 116. Such a configuration may provide a relatively robust and relatively reliable apparatus for retrieving fluid samples from a subterranean location.

Figure 4D:
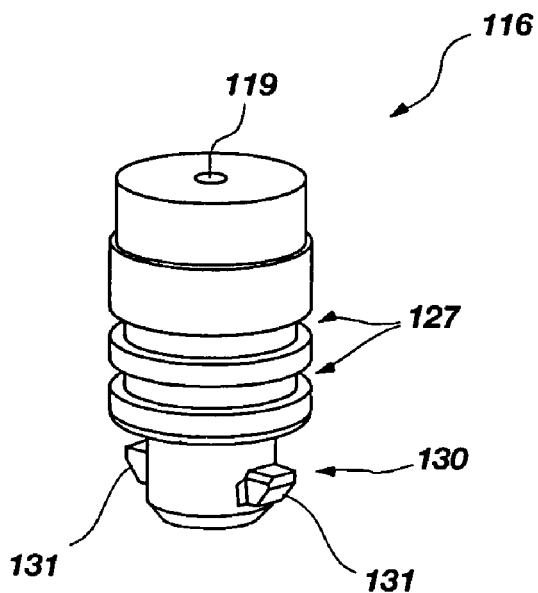
FIG. 4D shows a perspective view of a bottom plug according to the present invention.

For instance, as shown in FIG. 4D, locking structure 130 of bottom plug 116 may include at least one radially extending feature 131 for engaging or interlocking with a groove-shaped engagement feature 50 formed within the receiving member 38. In such a configuration, rotation and longitudinal displacement of the bottom plug 116 (by rotating the lysimeter 100) may effectively and selectively position and affix the at least one radially extending feature 131 within the groove-shaped engagement feature 50 of the receiving member 38 and also affix and position the lysimeter 100 in relation to the access casing assembly 10. In addition, at least one sealing element, shown in a currently preferred embodiment as two sealing elements 133 may be positioned to seal between the bottom plug 116 and the receiving member 38, upon coupling engagement therebetween. Further, bottom plug 116 may include port 119, as described in greater detail hereinbelow.

Optionally, the present invention contemplates that a bottom plug 116 may not be associated with lysimeter 100, may not include port 119, and may be placed within receiving member 38. In such a configuration, bottom plug 116 may be useful for maintaining the cleanliness of bore 35 of the body 34. Furthermore, bottom plug 116 may be removed prior to installation of access casing assembly 10 within a subterranean formation. Alternatively, if desirable, bottom plug 116 may remain within receiving member 38 during installation of access casing assembly 10 within a subterranean formation and may simply be removed (e.g., by wireline or other so-called "fishing" tool as known in the art) from receiving member 38 subsequent to installation of access casing assembly 10 within a subterranean formation.

Figure 4E:
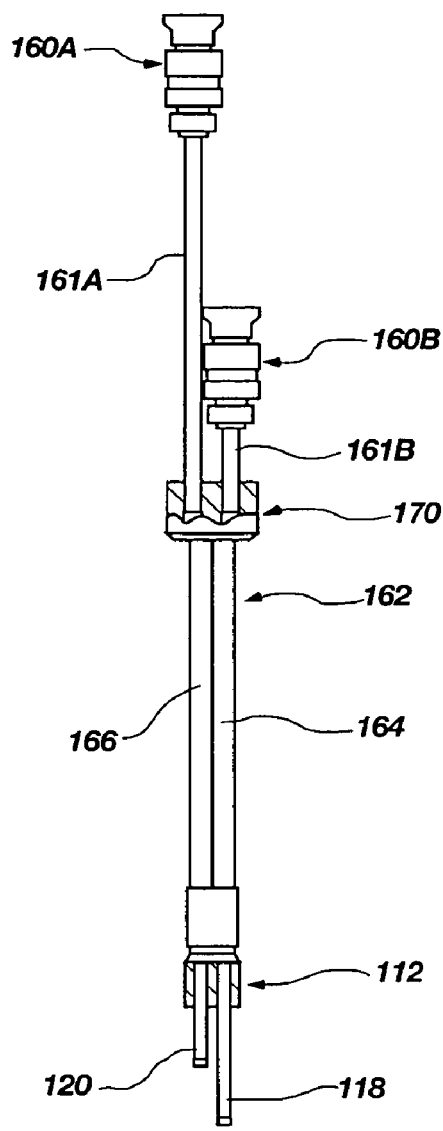
FIG. 4E shows a schematic view of a top plug and decoupling body according to the present invention.

Particularly, as shown in FIG. 4E, optionally, top plug 112 may be affixed to a decoupling body 162, having passageways 164 and 166 therein. Further, decoupling body 162 may include a pass-through retainer 170. Pass through retainer 170 may be configured for sealing decoupling body 162 without regard to the position of tubes 161A and 161B. Such a configuration may allow for adjusting of the position of coupling members 160A and 160B as desired (decoupled from vacuum/pressure tube 118 and sample tube 120, respectively), limited by the respective length of tubes 161A and 161B. Particularly, at least a portion of tubes 161A and 161B may be positioned within each of passageways 164 and 166 as desired and sealed to pass through retainer 170. Such a configuration may be advantageous for positioning 160A and 160B as desired so as to ease affixing coupling members 160A and 160B to other conduits or connecting devices as may be desired.

Figure 4F:
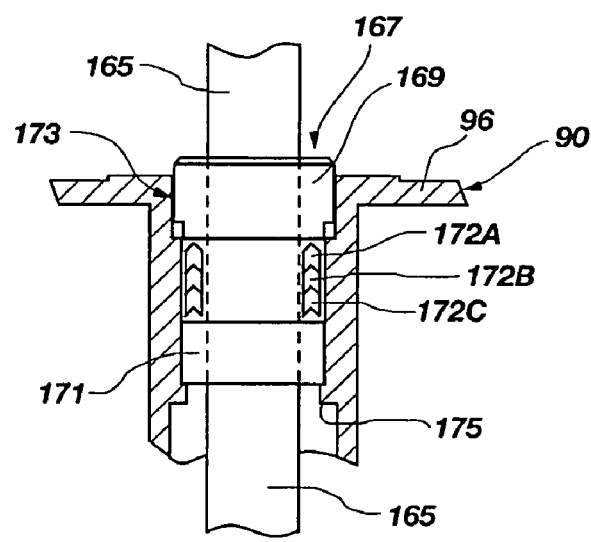
FIG. 4F shows a partial side cross-sectional schematic view of a device positioned within a port tube through a sealing plug.

In another aspect of the present invention, a sealing port may be configured for selectively sealing between a device and with respect to port tube 90. For example, as shown in FIG. 4F in a side cross-sectional schematic view, a sealing plug 167 may include at least one compressible (i.e., compliant or resilient) sealing element (shown as sealing elements 172A, 172B, and 172C) which may be configured for sealing against both an exterior of a device 165 to be installed within an access casing assembly (shown as installed within an internal bore of a port tube 90). In one embodiment, sealing elements 172A, 172B, and 172C may be commercially available from MSC INDUSTRIAL SUPPLY Company of Melville, N.Y., and may be known as a "V-packing set." In one exemplary embodiment, sealing elements 172A, 172B, and 172C may have an inside diameter (uncompressed) of about 1.125 inches and an outside diameter (uncompressed) of about 1.75 inches and a height (uncompressed) of about 1 inch.

In further detail, a top member 169 of sealing plug 167 may be structured for compressing sealing elements 172A, 172B, and 172C between lower member 171, which may be seated upon ledge 175 formed within port tube 90. More specifically, top member 169 may be tightened (i.e., toward lower member 171) via threaded surfaces 173 (referring to corresponding a threaded surface formed upon top member 169 and mating with a threaded surface formed within the bore of port tube 90) or other compressive mechanisms as known in the art. Such compression may cause (radially outward and inward) deformation or expansion of sealing elements 172A, 172B, and 172C so as to sealingly engage a bore surface of port tube 90 and an exterior surface of the device 165. Thus, device 165 may be positioned (raised or lowered) through the sealing plug while the sealing elements 172A, 172B, and 172C are not compressed and, when suitably positioned, top member 169 may be tightened so as to compress 172A, 172B, and 172C as discussed above. Such a configuration may be termed a "dynamic seal" and may provide a mechanism to selectively seal a device within an access casing assembly 10. Of course, the present invention contemplates that a selected level of compression may be provided (or adjusted) so as to cause sealing engagement between sealing elements 172A, 172B, and 172C and a bore surface of port tube 90 and an exterior surface of the device 165.

In addition, sealing elements 172 and 174 may be positioned so that, when lysimeter 100 is placed within access casing assembly 10, sealing engagement between the top plug 112 and the port tube may occur prior to sealing engagement of the bottom plug 116 with receiving member 38. Put another way, sealing elements 172 and 174 may initially seal against a bore surface of port tube 90 along a region thereof prior to engagement of bottom plug 116 within receiving member 38 and may maintain such sealing engagement (while moving, rotating, or both) as bottom plug 116 positively engages receiving member 38.

Such a configuration may be advantageous. For instance, if the porous filer 36 becomes dry, a fluid may be introduced within the access casing assembly 10 and may be pressurized by sealing the top plug 112 within the port tube while the bottom plug 116 is positioned so as to allow the fluid to pass into the bore 35 of the body 34. Thus, the porous filter 36 may be "primed" with a fluid without completely removing a device (e.g., such as a lysimeter 100) from the access casing assembly 10.

Figure 5A:
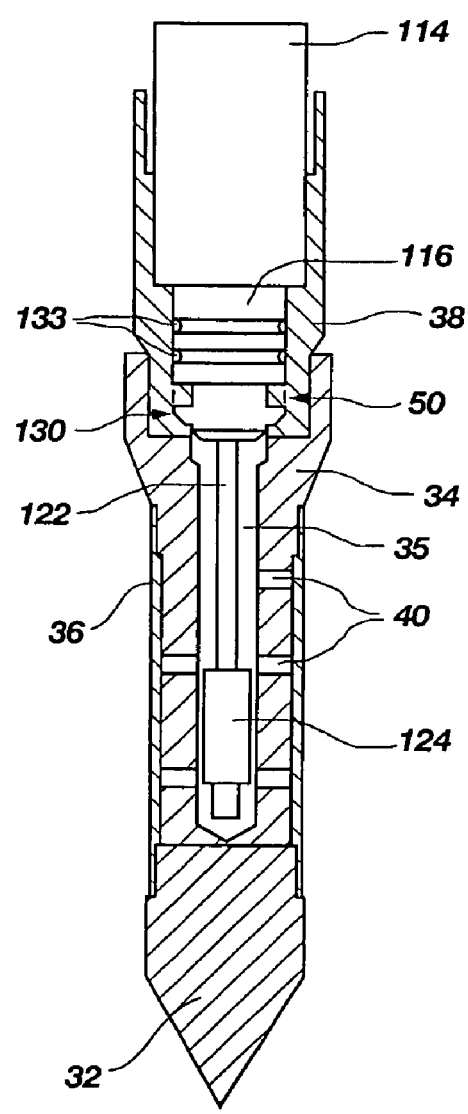
FIG. 5A shows a partial side cross-sectional view of an assembly including the lysimeter shown in FIGS. 4A-4C within a casing tip as shown in FIGS. 3A and 3B.

FIG. 5A shows, in a side cross-sectional view, at least one radially extending feature 131 of the bottom plug 116 engaging with a groove-shaped engagement feature 50 formed within the receiving member 38. As may be appreciated, receiving member 38 and bottom plug 116 may be sized and configured so that sealing elements 133 form a seal between the bottom plug 116 and the receiving member 38. Thus, upon installation of lysimeter 100 within access casing assembly 10, as shown in FIG. 5A, the draw tube 122 may position the check valve 124 proximate the lower extent of the bore 35 of the body 34. Such a configuration may allow for retrieval of substantially the entire contents of the bore 35 of the body 34, as described in greater detail hereinbelow.

Operation of the lysimeter 100, will now be described with reference to FIG. 5B, which shows a schematic representation of the lysimeter 100. Once the lysimeter 100 is installed within the access casing assembly 10, the vacuum/pressure tube 118 may be employed to remove gas from the reservoir portion 114, while sample tube 120 is plugged or blocked, thus drawing fluid from the bore 35 of the body 34 through the check valve 124, draw tube 122, port 119 of bottom plug 116, and into the reservoir portion 114. Then, gas may be introduced through the vacuum/pressure tube 118 to pressurize the reservoir portion 114. Pressurizing the reservoir portion 114, since check valve 124 may be configured to resist fluid flow from the bottom plug 116 thereforeward, may force fluid within the reservoir portion 114 and upwardly through the sample tube 120 for collection.

The lysimeter 100 may comprise, for instance, stainless steel for corrosion resistance, cost, and longevity. Since the lysimeter 100 may be placed within the access casing assembly 10 and may be removed therefrom, it may be reused, repaired, or a different instrument or device may be installed within the access casing assembly 10. In addition, lysimeter 100 may preferably extend above the flanged open end 92 of the port tube 90, when it is installed within access casing assembly 10 in a position suitable for operation thereof.

As shown in FIG. 5C, a protective cap 200 may be coupled (sealingly, if desired) to the port tube 90 and may inhibit exposure of the lysimeter 100 to the weather and may generally protect the lysimeter 100 from deleterious interaction with the environment. Further, as shown in FIG. 5D, the protective cap 200 may comprise two portions 200A and 200B. Such a configuration may allow for ease of access within an interior of access casing assembly 10 and may allow for placement of a device, such as lysimeter 100, to be positioned therein. Of course, protective cap 200 may be used for protection of the access casing assembly 10, without a device installed therein.

Figure 6A:
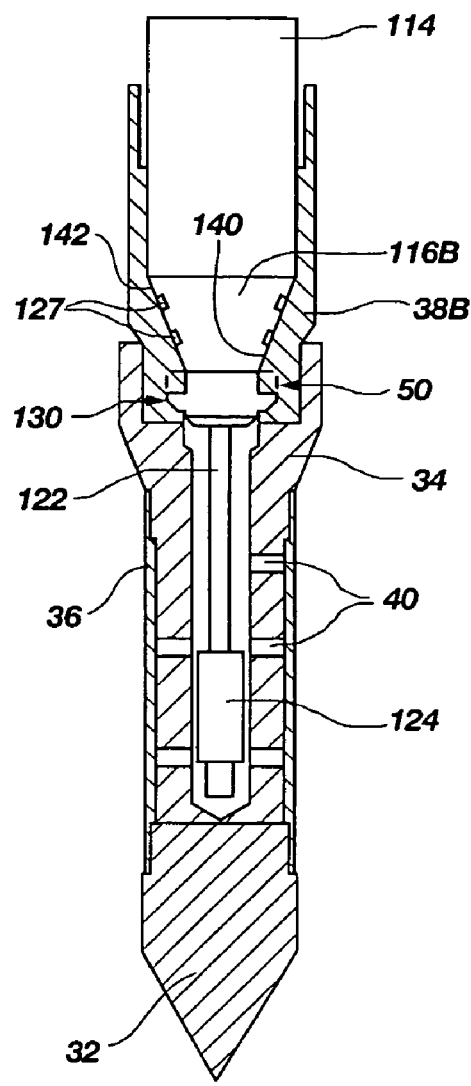
FIG. 6A shows a partial side cross-sectional view of an assembly including an alternative embodiment of a bottom plug within an alternative embodiment of a receiving member within a casing tip.

The present invention also contemplates alternative embodiments of a bottom plug and an associated receiving member. For instance, FIG. 6A shows, in a side cross-sectional view, that bottom plug 116B and receiving member 38B may be configured with complementary tapered surfaces 140 and 142, respectively. Preferably, at least one of tapered surfaces 140 and 142 may include at least one sealing feature 127, such as a groove configured for accepting a sealing element, such as an O-ring. Such a configuration may provide effective sealing engagement between tapered surfaces 140 and 142 when bottom plug 116B is engaged with receiving member 38B. In addition, the tapered surfaces 140 and 142 may inhibit or reduce undesirable pressure effects associated with installation of a bottom plug 116, as shown in FIGS. 4D and 5A. Particularly, such a configuration may reduce pressure build-up or development of "water hammer" type behavior, if any, during insertion of bottom plug 116 and may provide a suitable locking mechanism and sealing structure. Further, such a configuration may be configured for providing a selected level or magnitude of pressure build-up, which may be beneficial for wetting the porous filter 36 (FIGS. 3A and 3B).

Figure 6B:
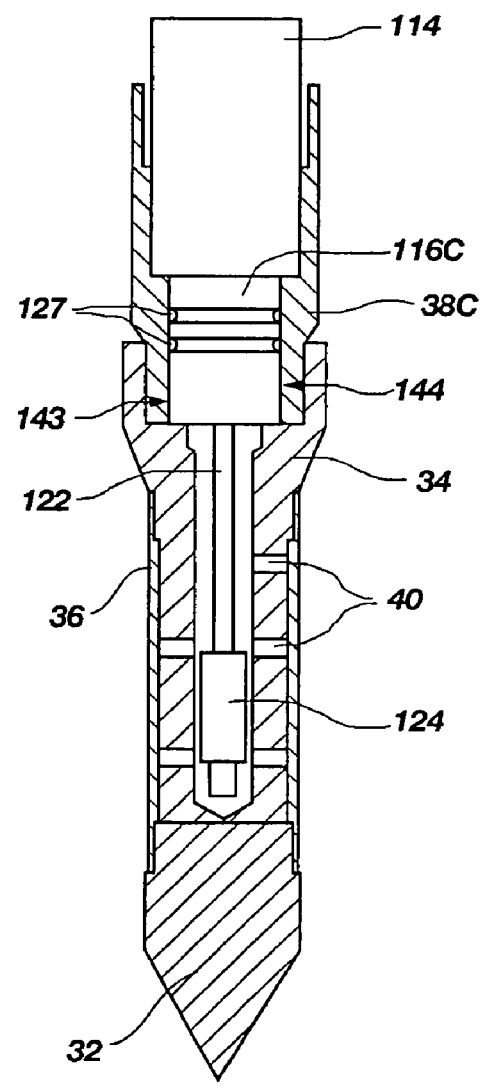
FIG. 6B shows a partial side cross-sectional view of an assembly including another alternative embodiment of a bottom plug within another alternative embodiment of a receiving member within a casing tip.

In another embodiment, as shown in FIG. 6B in a side cross-sectional view, receiving member 38C may be configured with a threaded surface 144, for accepting a complementary threaded surface 143 of bottom plug 116C. In one example, threaded surface 144 may comprise an API standard thread or other thread geometry as known in the art. Further, threaded surface 144 may comprise a tapered quick locking thread of a type commonly used to tighten so-called drill string pipe by way of ½ to ¼ of relative rotation between a complementary threaded member (not shown) and threaded surface 144. Further, at least one sealing feature 127, shown in a currently preferred embodiment as two sealing features 127 may be positioned to seal between the bottom plug 116C and the receiving member 38C, upon the bottom plug 116C and the receiving member 38C becoming coupled to one another. Although bottom plug 116 is described hereinbelow in relation to further aspects of the present invention, it should be understood that the present invention contemplates that the embodiments of bottom plugs 116, 116B and 116C may be used interchangeably, without limitation. Similarly, although receiving member 38 is described hereinbelow in relation to further aspects of the present invention, it should be understood that the present invention contemplates that the embodiments of bottom plugs 116, 116B, and 116C may be used interchangeably, without limitation.

Thus, the present invention contemplates that a device may positively engage or lock with respect to an access casing assembly 10 positioned within an intended region of a subsurface or subterranean formation. Such a configuration may allow for selective interaction with the intended region of the subterranean formation. For instance, although sampling of liquids or gases may be a typical function of a device installed within access casing assembly 10, other functions are contemplated by the present invention.

Accordingly, many types of devices may be coupled with the access casing assembly 10. For instance, seismic sources (e.g., orbital vibrators, among others), visual inspection devices, liquid or gas delivery (i.e., to the formation) devices, or other devices may be operably coupled within an access casing assembly 10 for interaction with an intended region of a subterranean formation. In another example, a geophone or hydrophone may be coupled with the access casing assembly 10. Generally, any sensor as known in the art may be coupled with the access casing assembly 10 for sensing a parameter or characteristic therewith. For example, any device of foreseeable utility for use within a subterranean formation may be adapted to be employed within an access casing assembly 10 of the present invention.

Accordingly, a suitably sized and configured device including a properly configured bottom plug in relation to a receiving member of an access casing assembly may be assembled therewith and operated to achieve a desired function or interaction with respect to a region of a subterranean formation. Further, assuming a suitable weight, in many configurations, a device installed within the access casing assembly may be installed and retrieved manually (e.g., by hand). Such a configuration may allow for inspection, repair, or replacement of subsurface instruments, devices, or equipment without a drill rig, additional excavation, drilling, or fear of contamination spread.

Further, it should be noted that although the drawings depict an access casing assembly 10 including casing sections 24 which are installed so as to form a substantially cylindrical central elongated cavity, the present invention is not so limited. Rather, the present invention contemplates that, either prior to placement within subterranean formation 8 or in response thereto, an access casing assembly 10 according to the present invention may include substantial curvature (i.e., along an arcuate path) in one or more regions thereof. Such curvature may be predictable or desirable. For instance, curvature of access casing assembly 10 may be desirable for placement of an access casing assembly 10 so as to avoid a particular region of a subterranean formation or to follow an intended installation path. Accordingly, a device of the present invention to be installed within such an access casing assembly may be structured to exhibit relative flexibility, so as to allow passing into an access casing assembly 10 having substantial curvature in one or more regions thereof. Further, an at least one engagement feature of the access casing assembly 10 and an at least one locking structure of a device for assembly therewith may be sized and configured for engaging despite relative misalignment, displacement, or deviation therebetween (in relation to a preferred engagement orientation and alignment). Put another way, there may be a range of alignments and orientations wherein the at least one engagement feature of the access casing assembly 10 and the at least one locking structure of a device for assembly therewith may engage one another.

Thus, in one example, a tensiometer may be installed within access casing assembly 10. A conventional tensiometer comprises a sealed chamber filled with water, a porous cup in communication with the chamber, and a pressure sensor (vacuum gauge) connected to the sealed water chamber. The porous cup is placed in a soil region, with good hydraulic contact between the water in the chamber and moisture in the soil surrounding the porous media. Relatively dry soil tends to pull water from the sealed chamber through the cup. The pulling effect of the dry soil places the water in the chamber under vacuum, thus creating a measurable sub-atmospheric pressure (partial vacuum) in the chamber. Higher moisture content in the soil may produce correspondingly less vacuum in the tube, and completely saturated soil may produce substantially zero vacuum, i.e., atmospheric pressure. In this way, a tensiometer may indicate a relative soil water content. Alternatively, when a tensiometer is installed below the water table, it may function as a piezometer, measuring a hydraulic head (i.e., pressure) of the water table at the point of placement.

In a further aspect of the present invention, a tensiometer may be provided having a chamber which is structured to fill with a fluid subsequent to contact therewith. In general, such a tensiometer may be configured for filling with fluid subsequent to placement within a subterranean formation. Such a configuration may be advantageous for eliminating the need for filling a chamber and maintaining the filled chamber of a tensiometer prior to communication within a subterranean formation. For instance, a tensiometer utilizing an electronic pressure transducer mounted at the point of measurement, which may eliminate the need for the long water columns taught by traditional tensiometer designs, as disclosed by U.S. Pat. No. 6,539,780 to Hubbell et al., the disclosure of which is incorporated, in its entirety, by reference herein, may be installed within access casing assembly 10 according to the present invention.

Figure 7A:
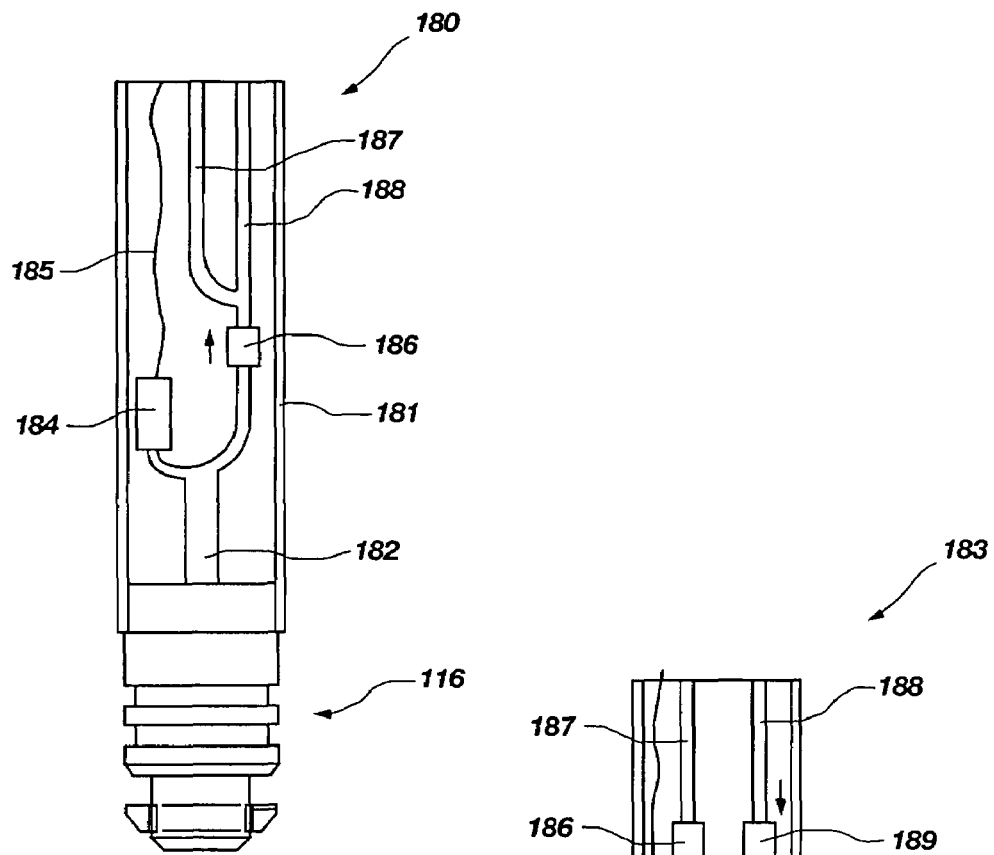
FIG. 7A shows a schematic representation of an embodiment of a tensiometer according to the present invention.

The present invention contemplates a tensiometer configured for engagement with the receiving member 38 of an access casing assembly and including a fluid containing chamber in communication with porous filter 36 and a pressure transducer for measuring the pressure or a relative change in pressure (in excess or below ambient atmospheric pressure) therein. In a particular example of a tensiometer of the present invention, a tensiometer apparatus may be specifically structured for advantageously coupling or temporarily affixing with an access casing assembly 10 of the present invention. As shown in FIG. 7A, a tensiometer 180, as shown in a schematic side cross-sectional view, may include a tubular body 181 affixed to a bottom plug 116 of the present invention, wherein the bottom plug 116 includes a single bore (not shown) therethrough for communication with bore 35 of body 34. Tensiometer 180 may further include conduit 182 in communication with the bore of bottom plug 116 and may be in further communication with both pressure transducer 184 and valve element 186 (e.g., check valve, electronic solenoid valve, etc.). Optionally, conduit 187 may be in fluid communication with conduit 188, proximate to valve element 186. Such a configuration may provide a fluid path for flushing fluid through at least one of conduit 188 and conduit 187, which may be useful for cleaning or clearing blockages therein. Pressure transducer 184 may be a strain gage-type, diaphragm pressure transducer as known in the art, or another pressure transducer as known in the art having communication lines 185 (e.g., wires) for communicating a pressure measurement as a voltage, for instance. More specifically, pressure transducer 184 may be configured for measuring a pressure (absolute or gage, in excess or below an ambient atmospheric pressure) or a relative change in pressure within conduit 182 while conduit is in communication with the bore 35 of body 34 of casing tip 16 (e.g., for a selected period of time). Valve element 186 may comprise a check valve configured for allowing fluid communication from conduit 182 to conduit 188 in response to a relatively low selected pressure differential (e.g., between about ¼-½ psid (differential), such as, for instance, ⅓ psid) or greater thereacross, while substantially preventing fluid communication from conduit 188 to conduit 182 for pressure differentials less than the selected pressure differential. Alternatively, valve element 186 may be configured for selectively allowing or preventing fluid communication from conduit 182 to conduit 188 as desired, for example by way of an electric signal communicated to valve element 186 (e.g., configured as a solenoid valve).

In further detail, as explained above, a fluid may be introduced within access casing assembly 10 (i.e., the bore 35 and, optionally, the receiving member 38 and casing section 24 attached thereto) for pressure testing thereof during placement thereof within a subterranean formation. Thus, a sufficient amount of liquid may be introduced within access casing assembly 10 so that positioning and coupling of tensiometer 180 within receiving member 38 may cause fluid therein to travel into the conduit 182. Thus, conduit 182 may form a chamber for holding the liquid, which may communicate with the subterranean formation through a port (not shown) in bottom plug 116. Further, the pressure within conduit 182 forming a chamber may be measured by pressure transducer 184.

Figure 7B:
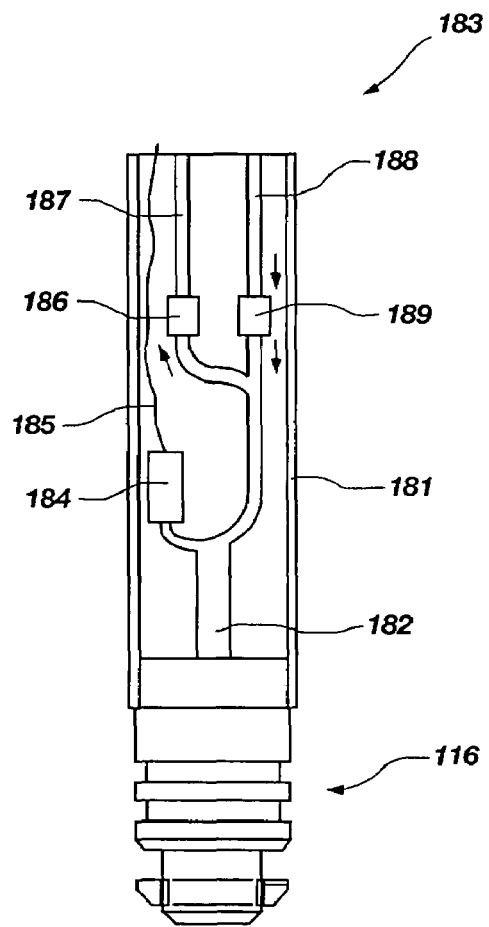
FIG. 7B shows a schematic representation of another embodiment of a tensiometer according to the present invention.

In a further embodiment of a tensiometer of the present invention, FIG. 7B shows a tensiometer 183 of the present invention. Tensiometer 183 may be generally configured as tensiometer 180 described above, including optional conduit 187, but may also include a valve element 189 (e.g., a check valve) configured for allowing fluid communication through conduit 187 when the pressure differential thereacross is at least about 15 psid. Such a configuration may allow for introducing additional fluid within conduit 182 (under pressure), if desired. Further, such a configuration may allow for flushing fluid through at least one of conduit 188 and conduit 187, which may be useful for cleaning or clearing blockages therein.

Figure 7C:
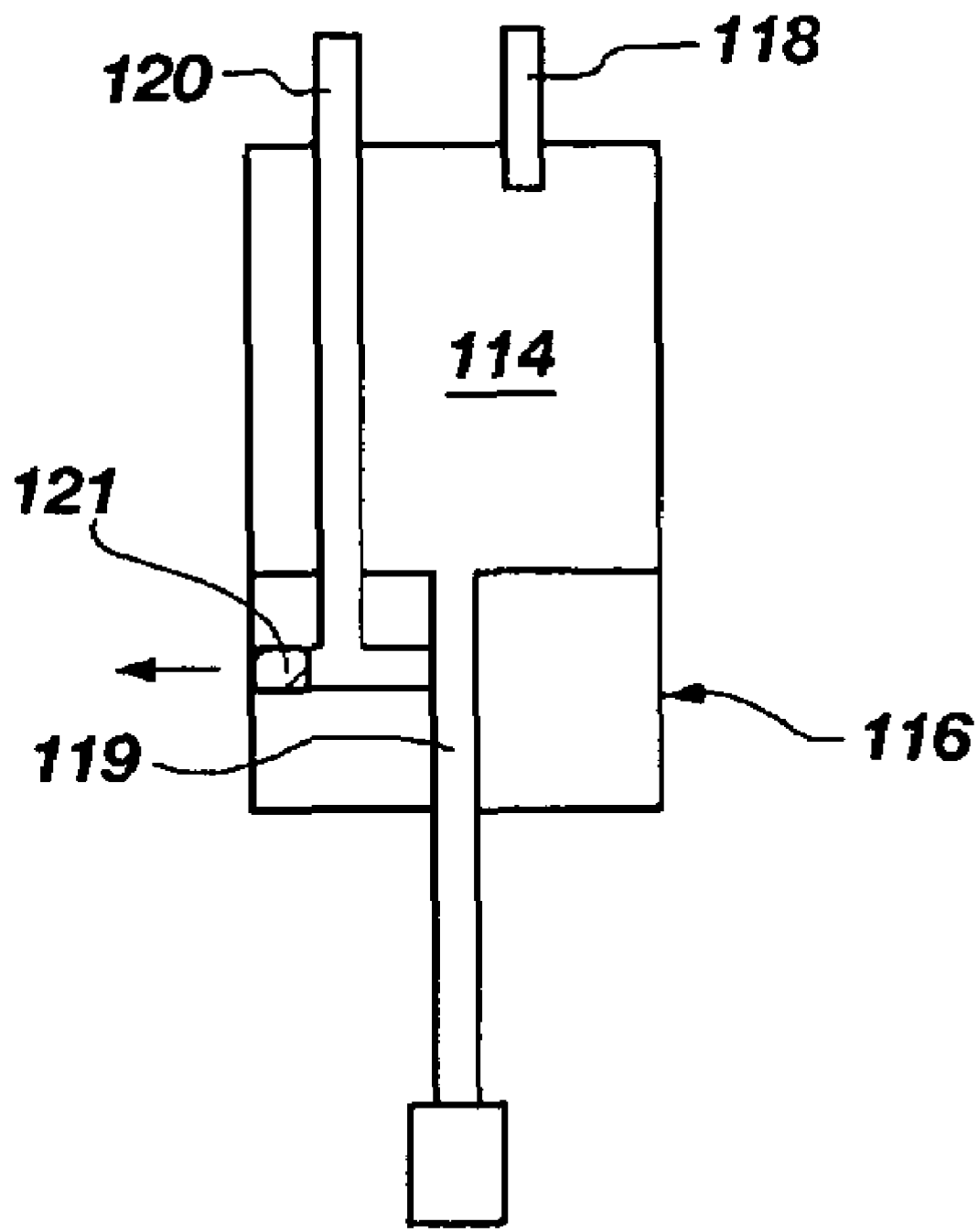
FIG. 7C shows a schematic representation of yet a further embodiment of a tensiometer according to the present invention.

Optionally, also as shown in FIG. 7C, a valve element 121 (e.g., a check valve) may be configured for allowing fluid to pass from port 119 to an exterior of bottom plug 116, but above two sealing elements 133 (FIG. 5A). Such a configuration may allow for release of a positive pressure within bore 35 of body 34, while allowing for proper tensiometer function. Accordingly, the present invention contemplates many different configurations for a tensiometer in accordance with the present invention.

Another type of geophysical monitoring device which may be installed within access casing assembly 10 is a vapor sampling device. The vapor sampling device may include a bottom plug 116 as described above, or variants thereof. Further, receiving member 38 may be configured, as described hereinabove with respect to a lysimeter, to sealingly connect the vapor sampling device to the receiving member 38 of the access casing assembly 10. The vapor sampling device may be configured for sampling a gas resident in the bore 35 of the body 34, the vapors having migrated through the porous filter 36 and into the bore 35. Alternatively, the sampling device may be an absorbing or adsorbing substance, such as, for instance, activated carbon, which may be exposed to the contents of bore 35 and subsequently returned to the subterranean formation's (i.e., earth's) surface for analysis.

A further type of geophysical or hydrogeologic monitoring device is an advective vapor sampling device, which may be typically employed for detecting volatile organic contaminants (VOCs). An advective vapor sampling device according to the present invention may include a bottom plug 116 or variants thereof as described above for selective securing and disengagement from an access casing assembly 10 of the present invention. The advective vapor sampling device may further include a desiccant/absorbent material which is mounted in fluid flowing relation relative to a pump assembly of conventional design.

Yet another type of geophysical monitoring device which may be positioned within access casing assembly 10 is a psychrometer. As known in the art, for example a thermocouple psychrometer or peltier type psychrometer may be configured for measuring the content or relative humidity of air. In one example, readings between two temperature measurement devices (e.g., thermometer, thermocouple, etc.), one having a wet bulb and the other having a dry bulb may be compared for measuring the content or relative humidity of air. According to the present invention, a psychrometer may include a locking structure, such as a bottom plug 116 of any of the embodiments encompassed by the present invention and as discussed hereinabove, for engagement with an engagement structure of an access casing assembly 10 of the present invention.

Accordingly, the present invention provides a relatively robust access casing assembly 10 that may be particularly useful for interaction, sampling, or measuring at least one characteristic of a subterranean formation, such as contaminated waste, as well as other uses. The access casing assembly 10 may be driven into difficult materials (e.g., hardened soils, concrete, steel, other metals, etc.) that may typically damage other tools. The various geophysical or hydrogeologic monitoring devices described herein are all operable to sense or otherwise identify various fluids, gases, or other characteristics of the subterranean location within which access casing assembly 10 is positioned.

As yet a further extension of the present invention, it should be understood that although the access casing assembly of the present invention is described hereinabove as including a single engagement feature for coupling with a single locking structure of a device positioned within an interior of the access casing assembly, the present invention is not so limited. Rather, the access casing assembly of the present invention may include at least one engagement feature for coupling with a respective at least one locking structure of a device positioned within an interior of the access casing assembly. Thus, the access casing assembly 10 of the present invention may include a plurality of engagement features for coupling with a respective plurality of locking structures of a device positioned within an interior of the access casing assembly. Such a configuration may provide increased structural rigidity and integrity of a device disposed within access casing assembly.

Figure 8:
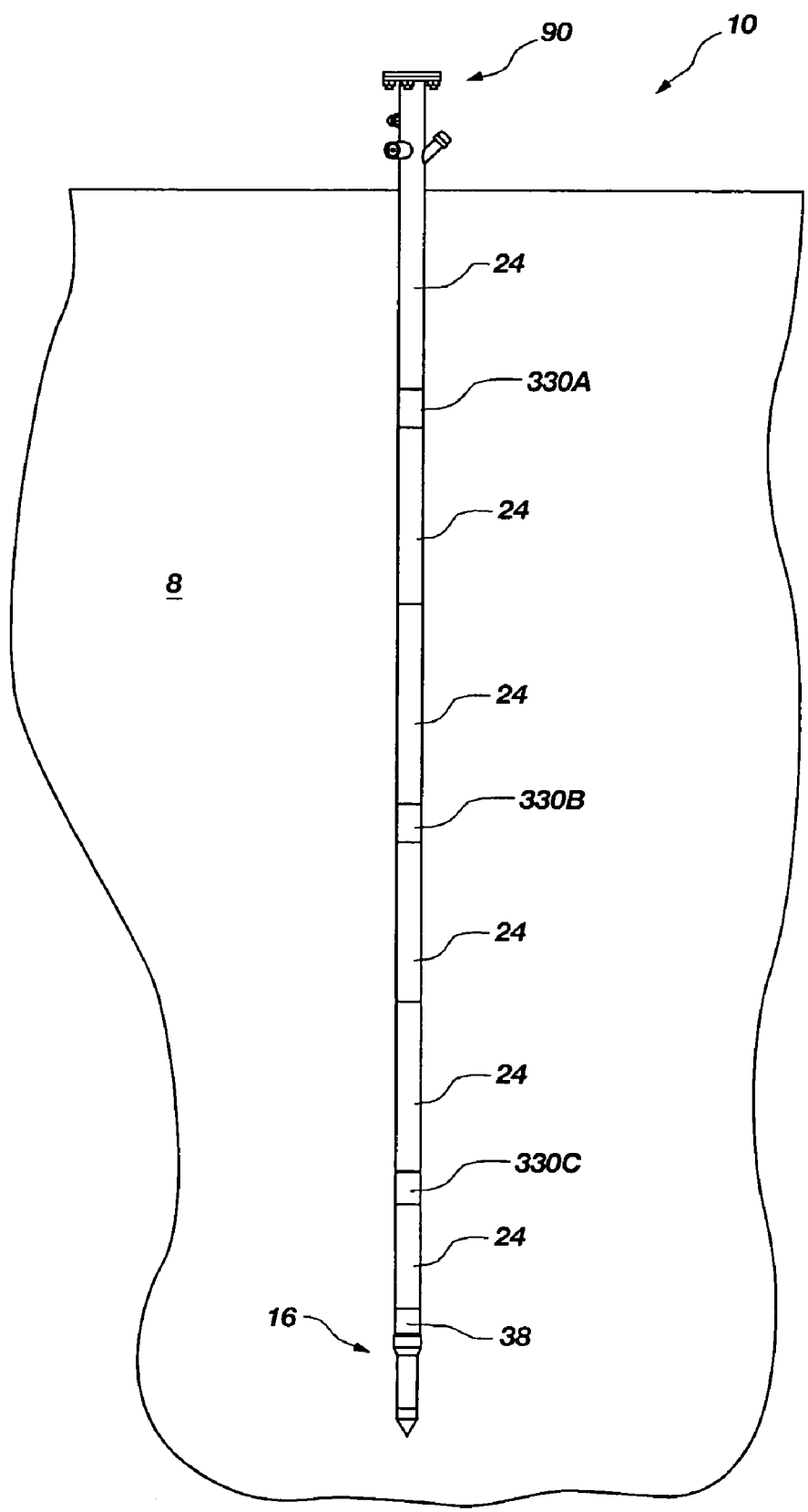
FIG. 8 shows a side schematic view of another embodiment of an access casing assembly of the present invention positioned partially within a subterranean formation and including a plurality of engagement hubs.

Further, it should be appreciated that a plurality of engagement features may be positioned along the length (i.e., longitudinally) of an access casing assembly of the present invention. For instance, FIG. 8 shows an access casing assembly 11, including a plurality of casing sections 24, casing tip 16, and port tube 90 disposed partially within subterranean formation 8, including a plurality of engagement hubs 330A, 330B, and 330C positioned along the length thereof, intermingled between the casing sections 24. Each of engagement hubs 330A, 330B, and 330C may be structured substantially identically or, alternatively, may be structured differently, without limitation. Each of engagement hubs 330A, 330B, and 330C may include threaded surfaces and, optionally, sealing features for affixation to and sealing against adjacent casing sections 24.

Figure 9A:
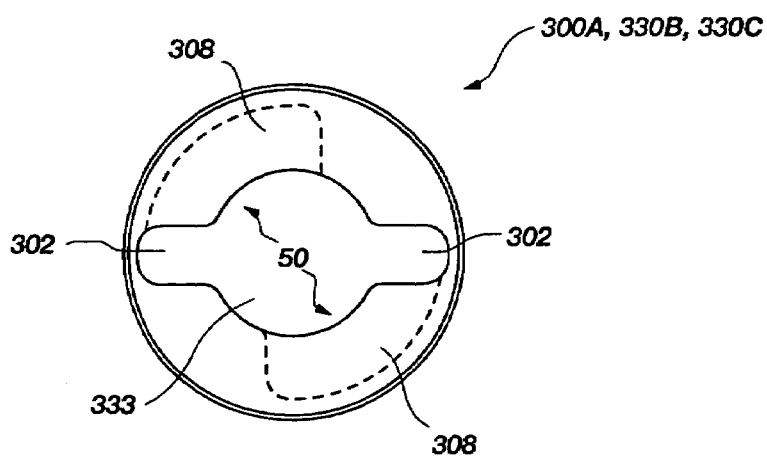
FIG. 9A shows a top elevation view of an embodiment of a receiving hub according to the present invention.
Figure 9B:
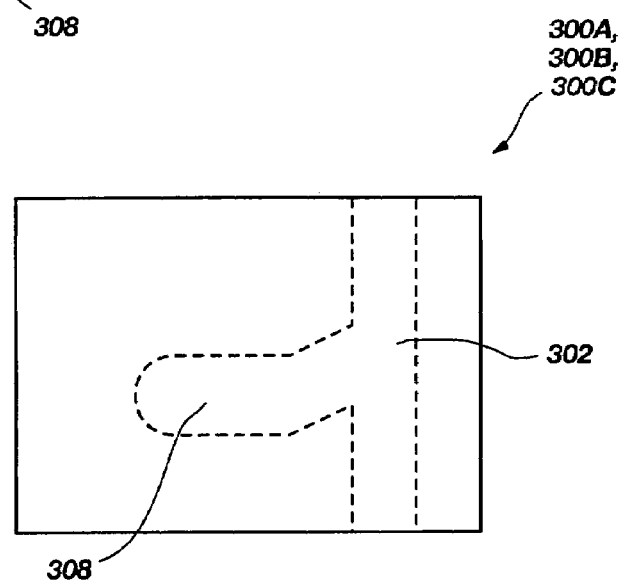
FIG. 9B shows a side schematic view of an embodiment of a groove formed in a receiving hub shown in FIG. 9A.
Figure 9C:
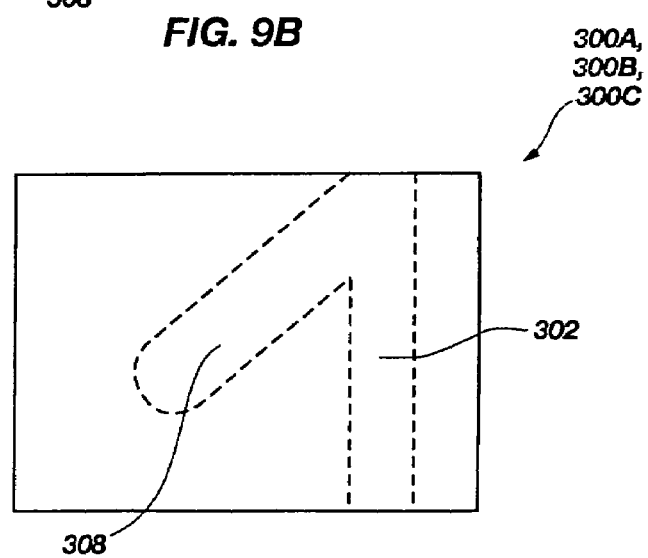
FIG. 9C shows a side schematic view of another embodiment of a groove formed in a receiving hub shown in FIG. 9A.

FIGS. 9A-9C show, in a top elevation view and two schematic side views, embodiments of engagement hubs 330A, 330B, and 330C of the present invention. As shown in FIGS. 9A-9C, each of engagement hubs 330A, 330B, and 330C may include keyways 302 extending therethrough. Accordingly, a device fitting generally within bore 333 of engagement hubs 330A, 330B, and 330C and having a locking structure, such as two radially protruding elements (not shown) fitting generally within keyways 302 may pass through each of engagement hubs 330A, 330B, and 330C. Optionally, of course, if the longitudinal position of the locking structure, such as two radially protruding elements (not shown) is appropriately aligned, the locking structure may be rotated into grooves 308.

Figure 10:
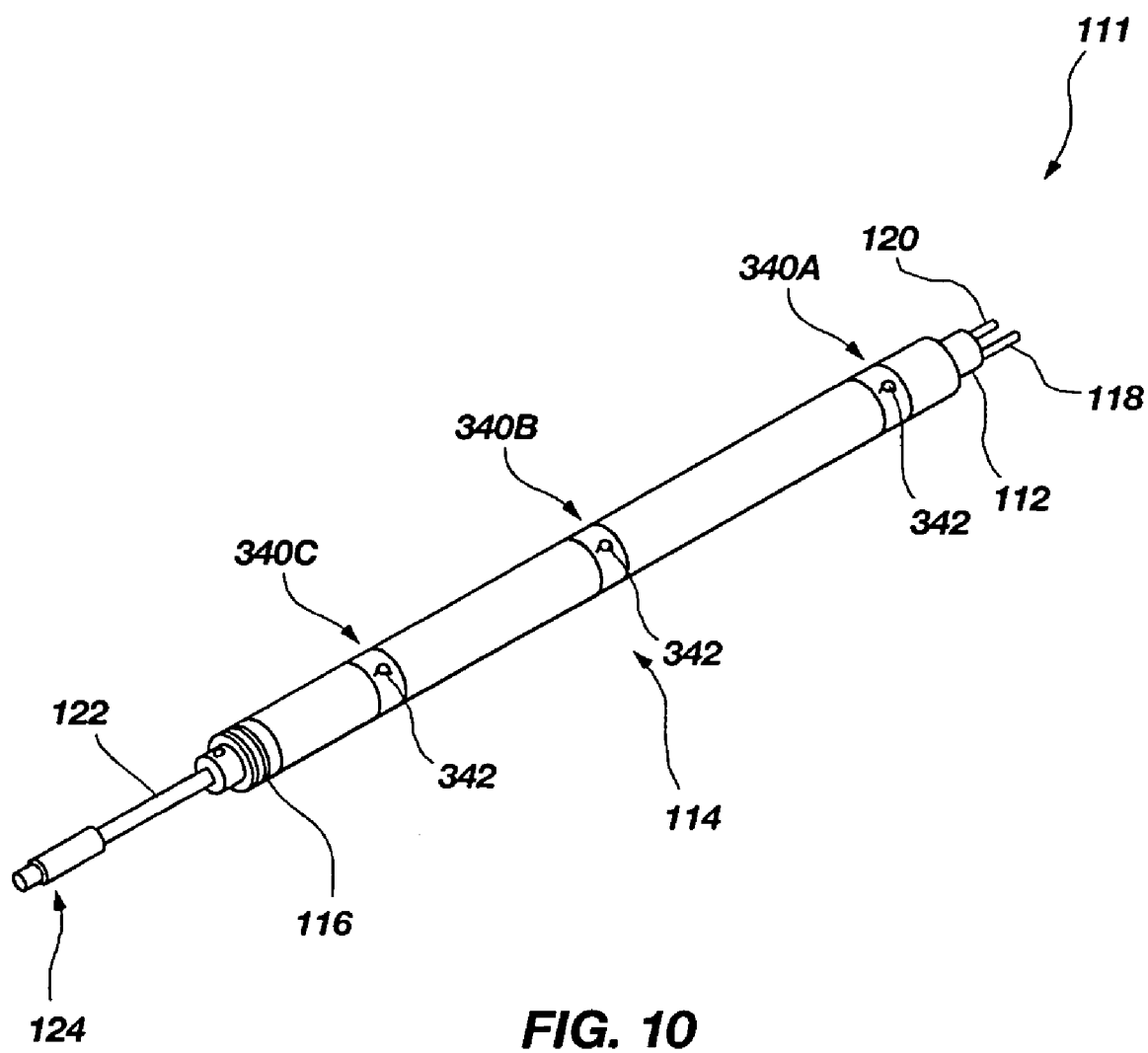
FIG. 10 shows a perspective view of a lysimeter of the present invention including a plurality of locking structures.

Thus, as a further aspect of the present invention, it is contemplated that a device, such as a lysimeter 111, as shown in FIG. 10 may be provided. Lysimeter 111 may be configured similarly, if not identically, with respect to lysimeter 110, as described hereinabove, but may also include a plurality of locking structures 340A, 340B, and 340C positioned along reservoir portion 114 for selectively engaging engagement hubs 330A, 330B, and 330C of access casing assembly 11. More specifically, locking structures 340A, 340B, and 340C may include at least one radially protruding element 342, respectively, configured for selective engagement with an engagement structure, such as a groove 308, of engagement hubs 330A, 330B, and 330C. It should be further noted that engagement of any of locking structures 340A, 340B, or 340C within any of engagement hubs 330A, 330B, and 330C may, selectively, allow for interaction with a portion of a subterranean formation proximate thereto. For example, a movable port or window may be configured for allowing interaction with a subterranean formation upon installation of a locking structure within an engagement hub, without limitation. Similarly, removal of any of locking structures 340A, 340B, or 340C from any of engagement hubs 330A, 330B, and 330C may close or prevent interaction with a subterranean formation. Of course, a manner or type of interaction (gas sampling, tensiometer measurement, liquid sampling, etc.) with a subterranean formation that may be selectively allowed or prevented may depend upon the type of device which is desired to be employed.

Thus, it may be appreciated that, as lysimeter 111 is disposed longitudinally downwardly within access casing assembly 11, locking structure 340C, if appropriately positioned, may be selectively engaged with any of engagement hubs 330A, 330B, and 330C. Further, locking structure 340B, if appropriately positioned may be selectively engaged with either of engagement hubs 330A or 330B. Also, locking structure 340C, if appropriately positioned, may be selectively engaged with engagement hub 330A. In addition, it may be appreciated that each of engagement hubs 330A, 330B, and 330C may respectively engage with locking structures 340A, 340B, and 340C, while bottom plug 116 may engage with receiving member 38. Such a configuration may provide a relatively secure and structurally rigid support and selective affixation of lysimiter 111 within access casing assembly 11.

Thus, subsurface instruments, devices, or equipment may be positioned (or selectively locked or engaged) at different positions or elevations within an access casing assembly according to the present invention. Further, the present invention contemplates that multiple instruments, devices, or instrument types may be engaged to, disengaged from, and used within the access casing assembly 10 substantially simultaneously. This feature may significantly reduce the cost of placing several conventional probes (or probe types) within an area to collect subterranean information.

It may further be appreciated that engagement of a locking structure with an engagement feature as described in any of the above embodiments may provide a communication path to the subterranean formation by opening a sealable port. Thus, communication with the subterranean formation may occur at any of the engagement hubs 330A, 330B, and 330C. Of course, if desired, sealing elements may be positioned and structured for effectively forming respective closed chambers in relation to engagement hubs 330A, 330B, and 330C for allowing selective sampling or other interaction with the subterranean formation in response to engagement of a locking structure therewith, respectively. Such a configuration may allow for relative flexibility in interacting with the subterranean formation at different positions within a single access casing assembly.

While the present invention has been described herein with respect to certain preferred embodiments, those of ordinary skill in the art will recognize and appreciate that it is not so limited. Rather, many additions, deletions and modifications to the preferred embodiments may be made without departing from the scope of the invention as hereinafter claimed. In addition, features from one embodiment may be combined with features of another embodiment while still being encompassed within the scope of the invention as contemplated by the inventors. Therefore, the invention is to cover all modifications, equivalents, and alternatives falling within the spirit and scope of the invention as defined by the following appended claims.

What is claimed is:

1. An access casing assembly for providing access to a subterranean formation, comprising:
   a casing portion comprising a plurality of casing sections operably coupled to form a central elongated cavity;
   a tip portion affixed to an end of the casing portion and including a porous filter through which liquid or gas may communicate with the central elongated cavity;
   a receiving member positioned proximate the tip portion forming a portion of the central elongated cavity, wherein the receiving member includes an engagement feature configured for selectively and lockingly engaging a locking structure of a device to be positioned at a sampling position within the access casing assembly;

wherein the access casing assembly is structured for placement at least partially within a subterranean formation by forcing the access casing assembly thereinto; and wherein the access casing assembly is configured for receiving the device in the sampling position within the access casing assembly after the access casing assembly is placed at least partially within the subterranean formation.

2. The access casing assembly of claim 1, wherein the engagement feature is configured for selectively and lockingly engaging the locking structure in an alignment which deviates from a preferred alignment.

3. The access casing assembly of claim 1, wherein the receiving member is structured for sealingly accepting the locking structure of the device.

4. The access casing assembly of claim 1, wherein at least a portion of one of the plurality of casing sections is substantially transparent.

5. The access casing assembly of claim 1, wherein the plurality of casing sections each have a first end and a second end, the first end of one casing section being configured for selectively coupling with the second end of another casing section forming a casing joint and wherein the casing joint includes a sealing feature for inhibiting pneumatic or hydraulic communication therethrough.

6. The access casing assembly of claim 1, wherein the porous filter comprises at least one of a sintered metal filter, a charcoal filter, a mesh filter, and a membrane filter.

7. The access casing assembly of claim 6, wherein the porous filter exhibits nominal pore openings of between about 0.1 micron and about 10 micron.

8. The access casing assembly of claim 6, wherein the porous filter comprises a sintered stainless steel filter.

9. The access casing assembly of claim 8, further comprising at least one sealing element is positioned between the porous filter and the body of the tip portion.

10. The access casing assembly of claim 8, wherein the porous filter is affixed to the body of the tip portion by way of at least one of welding, a threaded surface, soldering, and brazing.

11. The access casing assembly of claim 1, wherein the engagement feature of the receiving member comprises at least one of a threaded surface and a groove-shaped engagement feature.

12. The access casing assembly of claim 11, wherein the engagement feature of the receiving member comprises a bayonet-type connection structure.

13. The access casing assembly of claim 1, wherein the receiving member includes a tapered surface for engaging a correspondingly tapered surface of the device.

14. The access casing assembly of claim 13, wherein the receiving member is structured for sealingly engaging the device along a portion of the correspondingly tapered surface thereof.

15. The access casing assembly of claim 1, wherein the device comprises at least one of a lysimeter, a tensiometer, vapor sampling device, an advective vapor sampling device, a geophone, a vibration source, and a psychrometer.

16. The access casing assembly of claim 15, wherein the device comprises a lysimeter including:
a reservoir portion;
a bottom plug having the locking structure for selectively and lockingly engaging the engagement feature of the receiving member; and
a flow tube extending from the bottom plug and a check valve operably installed to the flow tube and configured for allowing fluid flow therethrough, toward the bottom plug.

17. The access casing assembly of claim 15, wherein the device further comprises:
a sealing plug having at least one sealing element wherein the sealing plug is configured for compressing the at least one sealing element and wherein the at least one sealing element is configured for sealing against a portion of the access casing assembly and a portion of the device positioned therein.

18. The access casing assembly of claim 1, wherein each casing section of the plurality of casing sections of the casing portion of the casing access assembly comprises at least one sealing feature structured for sealing against an adjacent, coupled casing section of the plurality of casing sections, respectively.

19. The access casing assembly of claim 18, wherein each casing section of the plurality of casing sections of the casing portion of the casing access assembly comprises a plurality of sealing features structured for sealing against an adjacent, coupled casing section of the plurality of casing sections, respectively.

20. The access casing assembly of claim 18, wherein each casing section of the plurality of casing sections of the casing portion of the casing access assembly comprises two sealing features structured for sealing with an adjacent casing section of the plurality of casing sections, respectively.

21. The access casing assembly of claim 19, wherein the plurality of sealing features comprises a plurality of O-rings.

22. The access casing assembly of claim 1, wherein the casing portion and the tip portion are sized and configured for placement into the subterranean formation by at least one of direct push, sonic drilling, and rotation.

23. The access casing assembly of claim 22, wherein the tip portion includes at least one of recesses and protrusions for facilitating placement of the access casing assembly into the subterranean formation by at least one of direct push, sonic drilling, and rotation.

24. The access casing assembly of claim 1, further comprising at least one engagement hub including an engagement feature for selectively and lockingly engaging at least another locking structure of the device to be positioned within the access casing assembly.

25. The access casing assembly of claim 24, wherein the at least one engagement hub comprises a plurality of engagement hubs, spaced along the longitudinal length of the casing portion of the access casing assembly.

26. An access casing assembly of claim 1, further comprising a drive shoe affixed to the casing portion and structured for coupling with a drive apparatus for forcing the access casing assembly at least partially into the subterranean formation.

27. The access casing assembly of claim 26, wherein the drive shoe further comprises:
a liquid port configured for introducing or removing a liquid into or from the central elongated cavity;
a gas port configured for introducing or removing a gas into or from the central elongated cavity, respectively; and
an abandonment port for introducing solid material or mixtures including solid material into or from the central elongated cavity.

28. The access casing assembly of claim 26, wherein the drive shoe includes a substantially cubical engagement end for coupling with a drive apparatus for placing the access casing assembly within the subterranean formation.

29. The access casing assembly of claim 26, wherein the access casing assembly is structured for allowing gas or liquid communication with the central elongated cavity substantially solely via the porous filter.

30. A method of interacting with a subterranean formation, comprising:
providing an access casing assembly including:
a casing portion comprising a plurality of casing sections operably coupled to form a central elongated cavity;
a tip portion assembled to an end of the casing portion, the tip portion including a porous filter; and
a receiving member positioned proximate the tip portion, wherein the receiving member includes an engagement feature configured for selectively and lockingly engaging a locking structure of a device positioned within the access casing assembly;
placing the access casing assembly at least partially into a subterranean formation;
placing the device within the access casing assembly after placing the access casing assembly at least partially into the subterranean formation and selectively engaging the device and the receiving member; and
interacting with the subterranean formation by operating the device.

31. The method of claim 30, wherein placing the device within the casing assembly and selectively engaging the device with the receiving member comprises selectively engaging at least one of a lysimeter, a tensiometer, a vapor sampling device, an advective vapor sampling device, a geophone, a vibration source, and a psychrometer with the receiving member.

32. The method of claim 30, wherein placing the casing assembly at least partially into the subterranean formation comprises at least one of direct pushing, rotating, and sonic drilling.

33. The method of claim 30, wherein:
placing the device within the casing assembly and selectively engaging the device and the receiving member comprises placing a lysimeter within the casing assembly and selectively engaging the lysimeter and the receiving member; and
further comprising providing vacuum pressure to a pressure tube of the lysimeter to pull a liquid through the porous filter from the subterranean formation and into a reservoir portion thereof; and providing a positive pressure within the reservoir portion to propel the liquid to a surface of the subterranean formation.

34. The method of claim 30, wherein placing the access casing assembly at least partially into a subterranean formation comprises causing the access casing assembly to exhibit curvature within at least one region thereof.

35. The method of claim 30, wherein placing the casing assembly at least partially into a subterranean formation comprises introducing a fluid into the central elongated cavity of the casing portion in contact with the porous filter.

36. The method of claim 35, further comprising pressure testing the central elongated cavity to substantiate that fluid or gas communication with the subterranean formation occurs substantially solely via the porous filter.

37. The method of claim 35, further comprising:
disposing a tensiometer within the casing assembly, the tensiometer having a chamber;
filling the chamber with the fluid within the central elongated cavity of the casing portion in contact with the porous filter;
measuring the pressure within the chamber over a period of time.

38. The method of claim 37, wherein filling the chamber with the fluid within the central cavity of the casing portion in contact with the porous filter comprises flowing the fluid through a valve element.

39. A method of interacting with a subterranean formation, comprising:
providing a casing assembly including:
a casing assembly having a casing portion comprising a plurality of casing sections operably coupled to form a central elongated cavity;
a tip portion assembled to an end of the casing portion, the tip portion including a porous filter;
a receiving member positioned proximate the tip portion, wherein the receiving member includes an engagement feature configured for lockingly engaging a locking structure associated with at least one device to be positioned within the casing assembly; and
at least one engagement hub forming a portion of the central elongated cavity and including another engagement feature configured for lockingly engaging another locking structure associated with the at least one device to be positioned within the casing assembly;
placing the casing assembly at least partially into a subterranean formation;
placing the at least one device within the casing assembly after placing the casing assembly at least partially into the subterranean formation;
positioning a sensor of the at least one device within the central elongated cavity of the casing assembly between the receiving member and the at least one engagement hub; and
interacting with the subterranean formation by operating the at least one device.

40. The method of claim 39, further comprising engaging the engagement feature of the receiving member with the locking structure associated with the at least one device and engaging the another engagement feature of the at least one engagement hub with the another locking structure associated with the at least one device.

41. The method of claim 39, further comprising engaging the another engagement feature of each of a plurality of engagement hubs of the casing assembly with corresponding locking structures of a plurality of locking structures associated with the at least one device.

42. The method claim 39, further comprising:
providing a plurality of engagement hubs;
placing a plurality of devices within the casing assembly; and
engaging each of the plurality of devices with a respective engagement feature of the plurality of engagement hubs of the casing assembly.

43. The method claim 42, further comprising operating the plurality of devices substantially simultaneously.

44. A method of sensing at least one characteristic of a subterranean formation, comprising:
placing an access casing assembly at least partially into a subterranean formation;
placing at least one sensor device within the access casing assembly after placing the access casing assembly at least partially into the subterranean formation;
engaging at least one engagement feature of the access casing assembly with at least one locking structure associated with the at least one sensor device;

establishing fluid communication between the at least one sensor device and the subterranean formation through a porous filter in the access casing assembly; and sensing at least one characteristic of the subterranean formation using the at least one sensor device.

45. The method of claim 44, further comprising:

removing the at least one sensor device from the access casing assembly after sensing the at least one characteristic of the subterranean formation and while the access casing assembly remains positioned at least partially within the subterranean formation;

placing at least one additional sensor device within the access casing assembly while the access casing assembly remains positioned at least partially within the subterranean formation; and sensing at least one additional characteristic of the subterranean formation using the at least one additional sensor device.

46. The method of claim 44, wherein placing at least one sensor device within the access casing assembly comprises placing at least one of a lysimeter, a tensiometer, a vapor sampling device, an advective vapor sampling device, a geophone, a vibration source, and a psychrometer with the access casing assembly.

47. The method of claim 44, wherein placing an access casing assembly at least partially into a subterranean formation comprises at least one of direct pushing and sonic drilling.

48. The method of claim 44, further comprising forming an exterior surface of the access casing assembly to be substantially smooth.

49. The method of claim 44, further establishing fluid communication between the at least one sensor device and the subterranean formation comprises establishing fluid communication between the at least one sensor device and the subterranean formation through a valve.

50. The method of claim 49, further comprising selectively actuating the valve.

* * * * *